(12) United States Patent
Wada et al.

(10) Patent No.: US 6,529,835 B1
(45) Date of Patent: Mar. 4, 2003

(54) HIGH THROUGHPUT METHODS, SYSTEMS AND APPARATUS FOR PERFORMING CELL BASED SCREENING ASSAYS

(75) Inventors: H. Garrett Wada, Atherton, CA (US); Steven A. Sundberg, San Francisco, CA (US)

(73) Assignee: Caliper Technologies Corp., Mountain View, CA (US)

( * ) Notice: Subject to any disclaimer, the term of this patent is extended or adjusted under 35 U.S.C. 154(b) by 196 days.

(21) Appl. No.: 09/604,785

(22) Filed: Jun. 26, 2000

Related U.S. Application Data

(63) Continuation-in-part of application No. 09/104,519, filed on Jun. 25, 1998.

(51) Int. Cl.[7] .............................................. G01N 33/50
(52) U.S. Cl. .......................................... 702/21; 702/19
(58) Field of Search .................... 156/655.1; 204/182.8, 204/299 R, 450, 451, 454, 601; 210/198.2; 216/33; 356/344; 417/48; 422/63, 82.05, 102, 104; 435/4, 91.2; 436/514; 548/236; 702/19, 21

(56) References Cited

U.S. PATENT DOCUMENTS

| | | | |
|---|---|---|---|
| 4,908,112 A | 3/1990 | Pace | 204/299 |
| 5,069,769 A | 12/1991 | Fujimiya et al. | 204/182.8 |
| 5,203,992 A | 4/1993 | Drouen | 210/198 |
| 5,447,612 A | 9/1995 | Bier et al. | 204/182.8 |
| 5,534,416 A | 7/1996 | Millard et al. | 436/34 |
| 5,627,643 A | 5/1997 | Birnbaum et al. | 356/344 |
| 5,750,015 A | 5/1998 | Soane | 204/454 |
| 5,804,436 A | 9/1998 | Okun et al. | 435/286.1 |
| 5,858,195 A | 1/1999 | Ramsey | 204/601 |
| 5,942,443 A | 8/1999 | Parce et al. | 436/514 |
| 5,965,410 A | 10/1999 | Chow et al. | 435/91.2 |
| 6,001,231 A | 12/1999 | Kopf-Sill | 204/454 |
| 6,046,056 A | 4/2000 | Parce et al. | 436/514 |
| 6,132,685 A | 10/2000 | Kereso | 422/104 |
| 6,136,171 A | 10/2000 | Frazier et al. | 204/450 |
| 6,149,787 A | 11/2000 | Chow et al. | 204/451 |

FOREIGN PATENT DOCUMENTS

| | | | | |
|---|---|---|---|---|
| EP | 0 581 412 | | 4/1993 | |
| WO | WO-99-34205 | * | 7/1969 | G01N/30/86 |

* cited by examiner

*Primary Examiner*—John S. Hilten
*Assistant Examiner*—Douglas N Washburn
(74) *Attorney, Agent, or Firm*—Ritter, Lang & Kaplan LLP

(57) ABSTRACT

Methods for determining a function of cells, which comprises a suspension of cells flowing along a first fluid channel. The cells have a first detectable property associated therewith, and wherein the cells produce a second detectable property upon activation of the function of the cells, the first and second detectable properties being distinguishable from each other. Levels of the first and second detectable properties are measured. The level of the second detectable property is compared to the level of first detectable property to determine the relative function of the cells.

42 Claims, 21 Drawing Sheets

HIGH THROUGHPUT METHODS, SYSTEMS AND APPARATUS FOR PERFORMING CELL BASED SCREENING ASSAYS

This application is a continuation-in-part of U.S. patent application Ser. No. 09/104,519, filed Jun. 25, 1998, which is hereby incorporated by reference for all purposes.

BACKGROUND OF THE INVENTION

Many aspects of biological research rely upon the ability to perform extremely large numbers of chemical and biochemical assays. Increasing the throughput of screening assays has allowed researchers to adopt a more generalized approach to the overall screening process, as opposed to a more rational, predefined process. For example, in the pharmaceutical discovery process, large libraries of different compounds are generally screened against defined target systems to determine whether any of those compounds have a desired effect on that system. Once a compound is identified to have the desired effect, it is then subjected to more rigorous analysis.

Many high-throughput screening assay systems rely upon entirely in vitro models of biological systems. This is due, at least in part, to the ability to accurately control substantially all of the parameters of the model system that is being assayed to permit correlation from assay to assay, such as the quantity and purity of reagents, the environmental conditions of the assay, the operator performing the assay, and the like. Specifically, variation of any of these parameters can produce widely varying results in the performance of a given assay.

In many cases, these in vitro systems have proven to be effective models of the biochemical system of interest, and have led to the identification of promising pharmaceutical candidate compounds. However, in many instances it is desirable to use a model system that is a closer representation of what actually occurs in more complex systems, e.g., in vivo. Cell-based systems offer a closer model to these relevant biological systems, and have generally been widely adopted as screening assays. While cell-based assays are generally preferred in screening applications, these assays have proven somewhat difficult to adapt to conventional notions of high-throughput and even ultra high-throughput screening assay systems.

As the multiplicity of cell-based assays increases, it becomes extremely advantageous to miniaturize the assay geometry. In the first instance, this miniaturization increases the efficiency of the assay by optimizing space utilization, reducing assay volumes, and consequently reduces reagent consumption and assay costs. For example, cells themselves, being a consumed reagent in such assays, are an expensive and perishable component of these assays, and quickly become a limiting influence on the application of these assays to high-throughput systems. Again, by miniaturizing assay geometries, the amount of this consumable reagent is reduced.

In addition to the economies of miniaturization, described above, a number of assay parameters become more and more critical as assay volumes are decreased. First, cells require a nutrient medium having a controlled pH in sufficient quantity to sustain their continued viability. Second, the cells need to be protected from desiccation, which is a particular problem in very small fluid volumes. Third, otherwise simple manipulations, such as reagent addition, rapid mixing and sampling become very difficult when dealing with extremely small fluid volumes. Further, continuous and accurate kinetic reading of assay results, e.g., monitoring of signals, during and after reagent or sample addition is a necessary element of many cell-based assays. Often these assay results come in the form of very small changes in signal levels from the cells, e.g., intracellular or membrane associated fluorescent signals. These small changes become increasingly difficult to detect as assay volumes are decreased and signal to noise ratios decrease.

Accordingly, it would generally be desirable to provide methods, devices and systems for performing cell based assays that are readily adaptable to high throughput screening applications, are readily automated, are easily repeated, and require less reagents and/or other assay components. The present invention meets these and a variety of other needs.

SUMMARY OF THE INVENTION

In a first aspect, the present invention provides methods of determining a function of cells, which comprises a suspension of cells flowing along a first fluid channel. The cells have a first detectable property associated therewith, and wherein the cells produce a second detectable property upon activation of the function of the cells, the first and second detectable properties being distinguishable from each other. The levels of the first and second detectable properties are measured. The level of second detectable property is compared to the level of first detectable property to determine the relative function of the cells.

The present invention also provides an apparatus for measuring a function of cells, comprising a body structure having a first fluid channel disposed therein. The first fluid channel is in fluid communication with a first source of a suspension of cells and the cells have a first detectable property associated therewith. The cells produce a second detectable property upon activation of the function of the cells, the first and second detectable properties being distinguishable from each other. The apparatus also optionally includes a material transport system for flowing the suspension of cells along the first channel and a detector for detecting and distinguishing the first detectable property from the second detectable property associated with cells within the first channel.

The present invention also provides methods of measuring a binding function of a cell, comprising a channel disposed in a first body structure. The channel comprises a first binding region and a non-binding region, the first binding region having a binding moiety immobilized on an interior surface of the first channel therein. A suspension of cells flows along a first channel, the cells comprising on their surfaces, a moiety specifically bound by the binding moiety. A relative velocity of cells flowing through the binding region is determined, relative to a velocity of cells flowing through a non-binding region. A decrease in the relative velocity is indicative of first binding in the binding region.

The present invention also provides an apparatus for measuring a binding function of a cell, using a body structure comprising a first channel disposed therein. The channel includes a binding region, a non-binding region, a binding moiety immobilized on an interior surface of the first channel in the binding region but not the non-binding region, a source of a suspension of cells in fluid communication with the first channel, a means for flowing the suspension of cells along the first channel, and a detection system for determining a relative velocity of cells flowing through the binding region compared to a velocity of cells flowing through the non-binding region.

BRIEF DESCRIPTION OF THE FIGURES

FIG. 1A illustrates the level of reference signal and function signal from a particular cell suspension over time, e.g., as it flows past a detection point.

FIG. 1B illustrates a comparison plot of detected function label versus reference label, and an approximate slope calculation for that comparison.

FIG. 1C illustrates the level of reference and function label in the same system, but where the assayed function is reduced over the system shown in FIG. 1A, e.g., in the presence of an inhibitor or absence of an enhancer.

FIG. 1D illustrates a comparison plot of the function and reference signals from FIG. 1C, and an approximate slope calculation for that comparison.

DETAILED DESCRIPTION OF THE INVENTION

I. Assay Methods

Figure 1:
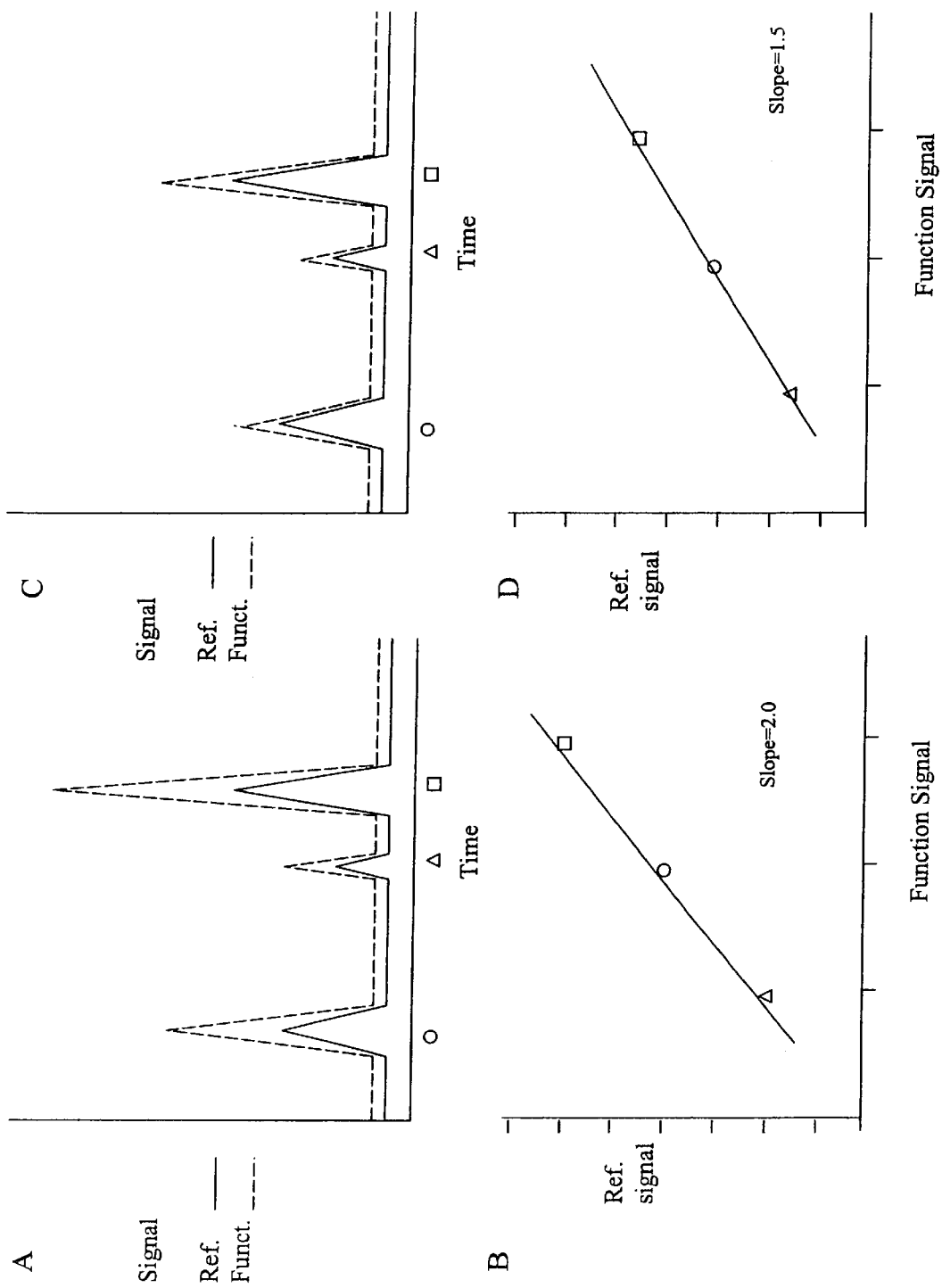
FIG. 1 is a simplified illustration the detected signal profiles obtained using the methods and systems of the present invention.

In general terms, the present invention provides methods, systems and apparatus for assaying biological functions. These methods, systems and apparatus are typically employed in assaying cells for a particular biological function, and in particularly preferred aspects, for screening test compounds for their effects, if any, on the biological function of cells. As used herein, the phrase "a function of cells" or "cellular function" generally refers to a selected biological activity or biological activities of cells. These functions include, without limitation, the full range of anabolic and catabolic reactions that occur within or at the surface of cells. Functions of cells range from specific predefined biochemical interactions, i.e., receptor/ligand binding, to the more general reactions and/or interactions, i.e., initiation of signaling cascades and overall cell viability. It will be readily appreciated that the cellular functions that may be assayed in accordance with the present invention are generally limited only by one's ability to detect that function or the results of that function. Preferred assayable functions include those that are generally considered to be pharmacologically relevant, are linked to a particular disease, disorder, or the like. Some general examples of these cellular functions include transport functions, i.e., ion channel activation, binding functions, i.e., ligand/receptor binding, nucleic acid hybridization, expression functions, i.e., gene expression and protein translocation, and overall cellular viability.

The present invention generally provides methods of assaying these cellular functions by flowing a suspension of cells along a first channel where the cells have a first detectable property associated with them. The first detectable property generally comprises a characteristic that is substantially uniformly associated with all of the cells that are being assayed. As such, this first detectable property functions as a "reference" label, to indicate the relative presence of cells within the assay system, e.g., that are being detected at any given time. As used herein, the phrase "substantially uniformly associated with cells in the suspension," means that the reference label will be present in/on all of the cells, or a selected subset of cells in a suspension at approximately the same level, e.g., with less than 20% variation, preferably less than 10% variation, and more preferably, less than 5% variation from one cell to another. The uniformity of the first detectable property among all cells allows for the relative quantitation of cells or subset of cells that are being interrogated at any given time in the assay, e.g., those that are within the field of detection.

By measuring the relative presence of cells within the measurement or detection region, the methods and apparatuses described herein provide measurements of cell function that are self-corrected for cell number. Thus, the methods of the present invention typically measure the reference and function labels from a plurality of cells, e.g., 2, 10, 100 or more, simultaneously.

The methods of the present invention are useful in measuring functions of virtually any type of cells, including, mammalian, bacterial, fungal, yeast, insect, and plant cells. In particularly preferred aspects, mammalian cells, e.g., CHO, THP-1 cells, blood cells, i.e., B cells, T cells, monocytes and neutrophils, and bacterial cells are used to screen for agents that affect these cell types, e.g., pharmaceutical agents, antibiotic agents, and the like.

In general, cell based assays can be performed in at least two different data regimes including discreet cell events and continuous cell events. With discreet cell events, the data typically includes a baseline level (e.g., fluorescence) with intermittent peaks (or drops) due to the passage of cells past the detector. The analysis software identifies each individual cell event and performs an analysis on the data associated with the cell event. With continuous cell events, cells are continuously passing by the detector so information on individual cells may be very difficult or impossible to obtain. The embodiments described herein utilize discreet cells events, however, the principles of the invention can be advantageously applied to other data regimes including continuous cell events.

A simplified example of the signal profile from both the reference and function signals and their comparison, is shown in FIG. 1. In particular, FIG. 1A illustrates the signal output from a scanner that detects and separately quantifies the reference signal (solid line) and the function signal (dotted line), e.g., a dual wavelength fluorescent detector. The signals are produced as a suspension of cells bearing the reference and function labels are flowed through a channel past the detector. The different peaks (denoted by the circle, triangle and square) represent different cells or groups of cells that pass the detector over time. The larger reference peaks correspond to larger groups of cells that are being detected at the particular time. FIG. 1B illustrates a comparison plot of the reference signal versus the function signal, where the slope (approximately 2.0) of the line is an indication of the relative function of each cell in the suspension.

FIG. 1C illustrates a similar plot of both reference and function signals as FIG. 1A, but in the presence of an inhibitor. As shown, the size of the function signal for each peak is reduced relative to the size of their corresponding reference peaks. This size differential is quantified in the comparison plot in FIG. 1D. In the presence of the inhibitor, the slope is reduced to 1.5, giving a quantitative indication of the amount of inhibition in the assay shown in FIG. 1C over that shown in FIG. 1A.

A variety of different detectable properties may be used as the reference label, in accordance with the present invention. For example, in some cases, inherent or native properties or characteristics of the cells are optionally employed as the first detectable property or reference label. While such inherent or native properties or characteristics, e.g., light scattering, flow characteristics, etc., may be used in some cases as the reference label, in preferred aspects, light scattering or other native characteristics are not used as the first detectable property, as the level and specificity of detectable signal from these characteristics is extremely low on a per cell basis. Instead, non-native labeling schemes are preferred for use in accordance with the present invention, for their ability to produce much higher and more specific signals. By "non-native" labeling scheme is meant the incorporation of a detectable property within a cell or cell line, that is not naturally associated with the cell or cell line.

Non-native reference labels include: associative labels, e.g., labeling groups that are added to the cells and which associate with a portion of the cells of interest; expressed labels, e.g., labeling groups that are constitutively expressed from a recombinant gene construct that is incorporated into the cells; and generated labels, e.g., labels that are produced as a result of some constitutive activity of the cells, e.g., energy utilization, generation of by-products, etc. In order to maximize sensitivity, reference labels are preferably selected from chromophoric labels (chromophores), chemiluminescent labels, fluorescent labels (fluorophores) or electrochemical labels, with energy emitting reference labels, e.g., fluorescent or chemiluminescent labels, being most preferred.

In certain aspects, associative labels are used as the first detectable property or reference label. In order to avoid interfering effects from the reference labels, it is generally desirable to select reference labels that do not have any effect on the cellular function that is to be assayed. In particular, associative reference labels are generally selected so as to avoid any activating influence on the cells, or any interaction with cell elements involved in the assayed function.

Examples of preferred reference labels include nucleic acid associating fluorescent labels. These labels generally associate with the nucleic acids that are present in the cells, and are therefore generally uniformly incorporated into all of the cells in the suspension. Commercially available examples of nucleic acid labels include, e.g., the SYTO series of dyes available from Molecular Probes, Inc., e.g., SYTO-17, which excite in the visible range of the spectrum, and may be selected depending upon a number of characteristics, including cell permeability, fluorescence enhancement upon binding nucleic acids, excitation and emission spectra, DNA/RNA selectivity and binding affinity. Protocols for incorporating these labels in the cells that are to be assayed are generally well known in the art, and/or are available from the manufacturer of the labels.

Alternatively, labels that associate with cell membranes, e.g., lipophilic labeling groups, or that associate with cell membrane components, e.g., cell surface proteins, in a passive or non-activating manner, are used to uniformly label all of the cells that are being assayed. A variety of membrane associative labels are commercially available and include, e.g., lipophilic fluoresceins such as acylaminofluorescein (tetrabromofluorescein, 5-dodecanoylaminofluorescein, 5-hexadecanoylaminofluorescein and 5-octadecanoylaminofluorescein), lipophilic rhodamines (octadecyl rhodamine B), alkylated coumarins, acridines and resorufin, and the like. These labeling materials are generally commercially available from, e.g., Molecular Probes, Inc. Again, labeling protocols are generally available from the manufacturers of these labels, and are well known to those of skill in the art.

Because the methods of the invention are self-correcting for cell concentrations, a wide range of cell concentrations are optionally used. However, in preferred aspects, the cell suspension is generally provided at a cell concentration that maximizes the sensitivity of the detection process, while minimizing negative effects of excessive cell concentrations, e.g., negative flow properties (i.e., clogging, excessive viscosity, excessive aggregation) excessive accumulation of deleterious by-products etc., that might effect assay results, and the like. As such, the cell suspensions are generally provided at cell concentrations between about $1 \times 10^5$ to about $1 \times 10^7$ per ml. Cell concentrations generally vary within this range, depending upon the nature of the channel through which the cells are being flowed during the assay process. For example, for narrower channels, more dilute cell suspensions are generally used, while for larger channels, higher cell concentrations can be tolerated. Of course for different cell types and sizes, concentrations outside this range are also envisioned. For example, for larger cell types, e.g., VB-2 cells, more dilute cell suspensions are used, while for smaller cell types, e.g., PBLs, more concentrated suspensions are used. The "suspensions of cells" discussed herein also encompasses cells that are adhered or immobilized to suspendable solid supports, e.g., beads (carbohydrate beads, latex microspheres, controlled porosity glass beads, and the like). Suspensions of beads carrying adhered cells are used in the same fashion as pure cell suspensions, as described herein.

Although described in terms of labels that are ubiquitously associated with the cells in the suspension, it should be understood that the reference label may be specific to a particular or distinct subset of cells within a given suspension, such that a function of that subset may be quantified in the overall suspension. As used herein, the phrase "distinct subset of cells" means a group of cells within a larger population of cells that has distinct functional, morphological, or genotypical characteristics, such that these cells can be separately identified and characterized from the remainder of the cell population. For example, in screening blood samples, reference labels may be selected that are specific to either white cells or red cells, or subsets thereof, e.g., labeled antibodies that are specific for B cells, T cells, monocytes, neutrophils, and the like. Function labels are then selected to indicate the level of a function of the particular cell subset.

In accordance with the present invention, the cells that are being assayed also include a second detectable property that results from the particular cellular function that is being assayed, also termed a function label. Function labels are usually selected depending upon the particular function that is being assayed. Types of assays and their function labels are generally described in greater detail, below.

As with the reference label, the function label may be an inherent or native characteristic that naturally results from the function of the cells, such as changes in the media composition, e.g., pH variations, and the like. Again, however, non-native labels and particularly energy emitting labels are preferred for use in accordance with the present invention. A variety of function labels are well known in the art, and are generally described in greater detail below.

Function labels are generally selected and/or provided such that they are readily distinguishable from the first detectable property, or reference label. The term "distinguishable" when used to describe the reference and function labels of the present invention, denotes two detectable properties that can be separately detected, and their levels separately quantified, using single or multiple detection systems. For example, the reference label may be detectable using an electrochemical label and detection system, while the function label is detectable using a fluorescent label and detection system. As a result, detection of the reference label does not substantially overlap or interfere with the detection of the function label. More typically, both the reference label and function label comprise fluorescent labeling groups. Again, however, the fluorescent reference and function labels are selected to be distinguishable from each other.

Fluorescent labeling groups are generally distinguishable from each other based upon one or more of their excitation spectra, emission spectra or fluorescent lifetimes. Specifically, the reference label may have an excitation maximum, e.g., wavelength of activation light required to cause the fluorescent groups to fluoresce, that is substantially different than the excitation maxima of the function label. By separately directing excitation light of different wavelengths at the cells, one could then determine the level of fluorescence resulting from the reference label versus the function label. Alternatively, the reference label and function label are selected to have distinguishable fluorescent emission maxima, e.g., they emit light or fluoresce at substantially different wavelengths. In operation, a single light source is directed at the cells. The fluorescent emissions from the cells are then passed through optical filters, which separate the different fluorescent emissions, which are then separately quantified. In selecting either distinguishable excitation or emission maxima, it is generally preferred that the excitation or emission spectrum of one label, e.g., the reference label, does not appreciably overlap with the excitation or emission spectrum of the other label. Specifically, while there is generally a maximum excitation or emission wavelength for different labels, there is typically a broader range of wavelengths at which there is some excitation or emission. Typically, labels are selected such that there is substantially no overlap between the excitation or emission spectra of the two labels, e.g., in detection of one label, less than 10% of the fluorescence is due to overlap from the other label.

Multi-wavelength detection schemes and systems have been described for use in a large number of different analytical systems, including macromolecular separations, e.g., sequencing of nucleic acids and the like (See U.S. Pat. No. 5,171,534), nucleic acid array scanning, and the like.

The first and second detectable properties, or the reference label and function label, are then measured in the flowing cell suspension. By comparing the level of function label to the level of reference label, one can identify and quantify any increases or decreases in the function of the cells, regardless of the number of cells that are detected. Specifically, by comparing the level of function label to the level of reference label, one can readily determine if an increase in the level of function label is a result of increased cellular function, or simply an increase in the number of cells that are detected. Specifically, the reference label provides an indicator of the number of cells that are subjected to measurement at a given time during the assay, while the function label, provides an indication of the amount of cellular function resulting from that number of cells.

Figure 2A:
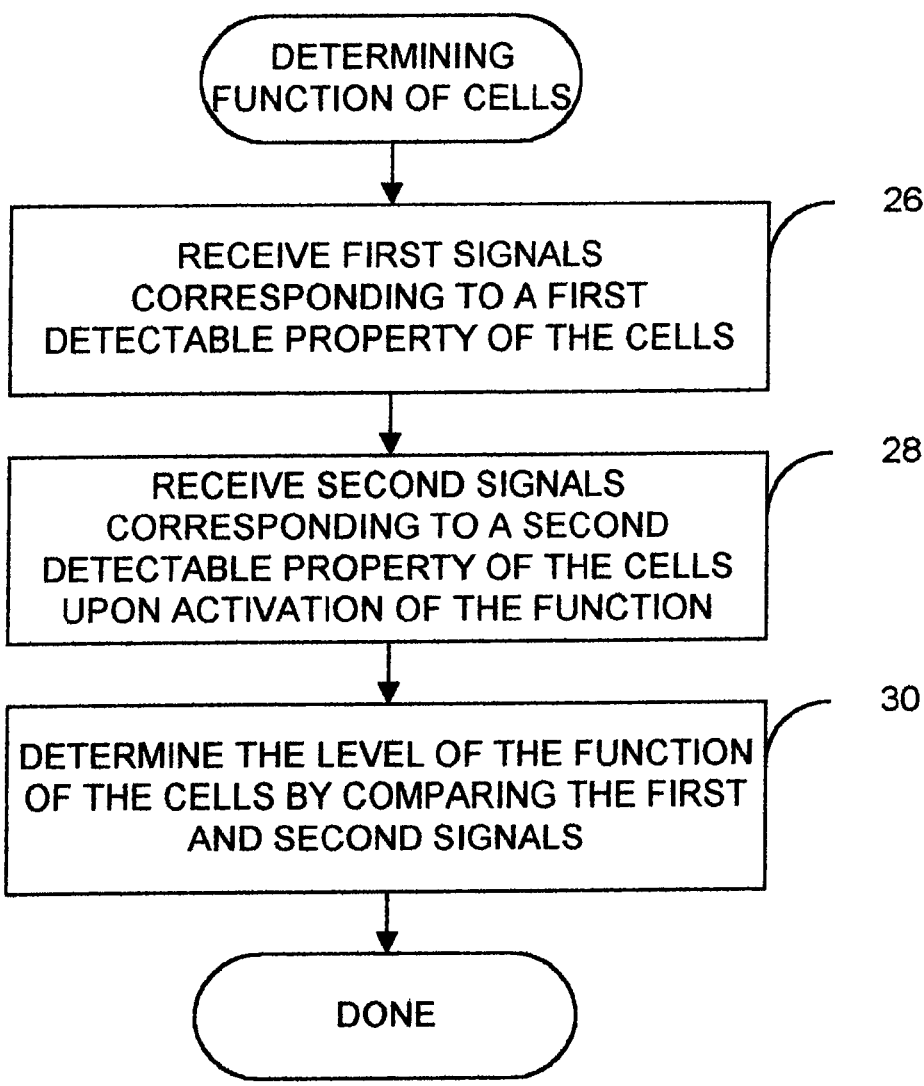
FIG. 2A shows a flowchart of a process of determining the level of function of cells and FIG. 2B shows a flowchart of a process of the determining binding function of cells.

FIG. 2A shows a flowchart of a process of determining the level of the function of cells that can be utilized in some embodiments of the invention. The function of the cells can be binding functions, transport functions, expression functions, viability, and the like. As with all the flowcharts herein, steps can be added, deleted, reordered, and combined without departing from the spirit and scope of the invention.

At a step 26, first signals corresponding to a first detectable property (e.g., from a reference label) of the cells is received. The cells are in a suspension flowing along a fluid channel and the first signals indicate that the cells have flowed to a detection point in the fluid channel.

Second signals corresponding to a second detectable property (e.g., from a function label) produced by the cells upon activation of the function of the cells are received at a step 28. The second signals also indicate that the cells have flowed to a detection point in the fluid channel. At a step 30, the level of the function of the cells is determined by comparing the first and second signals. Typically, the level of the function of the cells is also displayed to a user.

In some embodiments, the first and second signals are compared by calculating a ratio of the first and second signals. The ratio is then indicative of the level of the function of the cells. Additionally, the fluid channel can include a test compound so that the effect of the test compound on the level of the function of the cells can be determined. For example, the level of the function of the cells in the presence of the test compound can be compared to a reference level of the function of the cells, such as where the reference level of the function of the cells is in the absence of the test compound. The effects of different test compounds can be analyzed by serially introducing the different test compounds into the fluid channel, measuring the signals from the cells and determining the effect of each of the different compounds on the function of the cells, which can also be displayed to a user.

The ability to quantitatively determine cellular function within a single channel using the presently described methods, provides significant advantages over previous cell-based assay systems, e.g., flow cytometry, where optimal assay results are obtained from individual separated cells, rather from larger numbers of cells. Because separation of individual cells is not necessary to practice the methods described herein, these methods also require much less sophisticated equipment, e.g., fluid handling, detection systems, and the like. Data acquisition from individual cells further suffers from problems of cell to cell variations, and the like. In particular, in flow cytometry methods, large numbers of individual cells must be individually assayed in order to observe data trends, whereas the methods of the present invention observe and detect such trends much more quickly, e.g., with each data point.

Other cell based assay systems, such as flow cytometry, also suffer from an inability to easily add affector agents and kinetically monitor the cell response. The methods and apparatuses of the present invention, on the other hand are readily employed in adding affector agents and monitoring their affects, kinetically, on the cells in the assay. Specifically, incubation times of cells and affector agents are generally altered by simply altering the amount of incubation time prior to detection. In the methods and apparatuses described herein, this is simply done by either altering the length of the incubation channel, varying the point along the detection channel at which the assay results are detected, or slowing the flow rate along the reaction channel. Kinetics are also easily monitored by incorporating additional detectors, e.g., one or more additional detectors, at different points along the reaction channel.

Other cell-based assays, e.g., those carried out in multi-well plates, also suffer from substantial variations due to variations in the number of cells present within the reading area of the detection system. In particular, this can occur when affector agents are rapidly added, which can dislodge cells from the surfaces of the wells, causing those cells to move into and out of the reading area.

As noted above, the assay methods of the present invention are typically used in screening test compounds for their ability to affect cellular functions. In performing these screening assays, the cells that are to be assayed are exposed to different test compounds or conditions. In screening libraries of compounds, these compounds are typically separately introduced into the flowing suspension of cells. The relative level of a particular cellular function is then compared to a control system, e.g., the cells in the absence of the compound or condition, to determine whether the compound or condition has an effect on the cellular function. For example, where the level of relative cellular function decreases in the presence of a compound, it will be presumed that the compound possesses an inhibitory activity toward the cellular function. Conversely, where a cellular function is increased in the presence of the compound, it is assumed that the compound provides an enhancing activity to the cellular function. In either event, compounds that show some effect on cellular function are then subjected to more pointed analyses to elucidate their precise activity with respect to the cellular function.

II. Assay Types

A. Assaying Relative Cellular Function

As noted above, the methods and systems of the present invention are useful in assaying for virtually any cellular function, provided that either the function or a result of the function is independently detectable. In biological applications, and particularly pharmaceutical research, a number of specific types of assays are generally used as screening models for the identification of potential drug candidates, or "lead compounds." The assay types most frequently used in these screening operations generally include transport assays, binding assays, viability assays and expression assays.

1. Transport

In a first aspect, the methods and systems of the present invention are used in assaying cellular transport functions, i.e., ion flux, and intracellular pH regulation. In particular, cellular transport channels have been generally shown to be responsive to important cellular events, e.g., receptor mediated cell activation, and the like. For example, G-protein coupled receptors have been shown to directly or indirectly activate or inactivate ion channels in the plasma membrane or endosomal membranes of cells, thereby altering their ion permeability and thus effecting the excitability of the membrane and intracellular ion concentrations. See, Hille, Ionic Channels of Excitable Membranes, Sinauer Assoc. (1984).

In accordance with this aspect of the present invention, therefore, the function specific label comprises an indicator of the level of a particular intracellular species. In particularly preferred aspects, the intracellular species is an ionic species, such as $Ca^{++}$, $Na^+$, $K^+$, $Cl^-$, or $H^+$ (e.g., for pH measurements). A variety of intracellular indicator compounds are commercially available for these ionic species (e.g., from Molecular Probes, Eugene Oreg.). For example, commonly used calcium indicators include analogs of BAPTA (1,2-bis(2-aminophenoxy)ethane-N,N,N',N'-tetraacetic acid), such as Fura-2, Fluo-2 and Indo-1, which produce shifts in the fluorescent excitation or emission maxima upon binding calcium, and Fluo-3 and Calcium Green-2, which produce increases in fluorescence intensity upon binding calcium. See also, U.S. Pat. No. 5,516,911. Sodium and potassium sensitive dyes include SBFI and PBFI, respectively (also commercially available from Molecular Probes). Examples of commercially available chloride sensitive indicators include 6-methoxy-N-(sulfopropyl)quinolinium (SPQ), N-(sulfopropyl)acridinium (SPA), N-(6-methoxyquinolyl)acetic acid, and N-(6-methoxyquinolyl)acetoethyl ester (Molecular Probes, Inc.), all of which are generally quenched in the presence of chloride ions.

In a related aspect, the function specific indicator is an intracellular pH indicator compound. Specifically, intracellular pH changes have been found to be associated with biologically and pharmaceutically important cellular events, including cell proliferation, apoptosis, fertilization, malignancy, ion transport, drug resistance, lysosomal storage disorders, and Alzheimer's disease. A variety of indicator compounds are commercially available to indicate the intracellular pH of cells, and are readily applicable to the present invention as indicators of cellular function. Examples of these pH indicators include, e.g., SNARFL, SNARF, BCECF, and HPTS, available from Molecular Probes, Inc.

In operation, a suspension of cells that is to be assayed is flowed along a channel. The cells include a reference label as described above, i.e., SYTO dyes available from Molecular Probes. The cells are also treated with an intracellular indicator of the level of the species for which relative transport levels are to be determined, and which indicator is distinguishable from the reference label. As a specific example, the cells are optionally stained with, e.g., SYTO-17 as a reference label. SYTO-17 is a red nucleic acid dye that is generally excited by light at approximately 621 nm, and which emits light at approximately 634 nm. The cells are also optionally treated with an intracellular calcium indicator, e.g., Fluo-3, also available from Molecular Probes, which is excited at 488 nm and emits at approximately 530 nm. The two labels are easily distinguishable based upon their differing fluorescent emission maxima.

At a point in the channel, the cells are illuminated with a broad spectrum of light, e.g., light that encompasses the excitation maxima of both the SYTO-17 and Fluo-3 labels. Emitted fluorescence is then passed through optical filtering systems that separate and separately detect the SYTO-17 fluorescence and the Fluo-3 fluorescence. The levels of fluorescence from each dye are then compared (see e.g., FIG. 10). For example, the comparison optionally includes plotting the level of reference label versus the level of function label. Over the course of the assay, a number of separate data points are gathered that represent different cells or groups of cells that are detected. These are plotted and the slope of the resulting line is calculated. Changes in this slope are indicative of changes in the level of the function that is being assayed (see, e.g., FIGS. 11A–11E and FIG. 13).

2. Binding a) Generally

In an alternate aspect, the methods and systems of the present invention are used in assaying cellular binding functions, such as ligand-receptor binding, nucleic acid hybridization, antigen/antibody binding, cell-cell interactions, and the like. As with transport functions, cellular binding functions are often necessary precursors to a variety of cellular functions. Specifically, many biological responses are often triggered and/or controlled by the binding of a receptor to its ligand. For example, interaction of growth factors, i.e., EGF, FGF, PDGF, etc., with their receptors stimulates a wide variety of biological responses including, e.g., cell proliferation and differentiation, activation of mediating enzymes, stimulation of messenger turnover, alterations in ion fluxes, activation of enzymes, changes in cell shape and the alteration in genetic expression levels. Accordingly, control of the interaction of the receptor and its ligand may offer control of the biological responses caused by that interaction. As noted, included within these biological functions controlled by binding reactions are many transport functions, e.g., G-protein linked receptor activation, as set forth above. Accordingly, these binding functions may be detected by detecting the downstream event for which binding is a precursor, e.g., enhanced or decreased transport function, expression of receptor linked reporter label, protein translocation, or by detecting actual binding of cells with a binding agent, e.g., a ligand, nucleic acid or the like, through the inclusion in the ligand of a binding indicator, e.g., fluorescent resonance energy transfer dyes (FRET), molecular beacons, etc. For example, in the case of cell-cell interactions, detection of binding may be accomplished by labeling the cells' surfaces with both elements of appropriate FRET dyes, e.g., energy donor and energy acceptor. Upon cell-cell binding, these elements are placed in sufficient proximity for energy transfer, allowing their detection.

Alternatively, fluorescence polarization detection methods are used to detect binding of relatively small molecules, e.g., ligands, antibodies, etc., to relatively large structures, e.g., cells. Fluorescence polarization assays for use in microfluidic systems are generally described in Provisional U.S. Application No. 60/088,650, filed Jun. 8, 1998, incorporated herein by reference.

A variety of other detection/labeling mechanisms are also available for detecting binding of one molecule, e.g., a ligand or antibody, to another molecule, e.g., a cell surface receptor. For example, a number of labeling materials change their fluorescent properties upon binding to hydrophobic sites on proteins, e.g., cell surface proteins. Such labels include, e.g., 8-amino-1-naphthalene sulfonate (ANS), 2-p-toluidinylnaphthalene-6-sulfonate (TNS) and the like. Alternatively, detectable enzyme labels are utilized that cause precipitation of fluorescent products on solid phases, i.e., cell surfaces are optionally used as function indicators of binding. For example, alkaline phosphatase substrates that yield fluorescent precipitates are optionally employed in conjunction with alkaline phosphatase conjugates of cell binding components. Such substrates are generally available from Molecular Probes, Inc., and are described in, e.g., U.S. Pat. Nos. 5,316,906, 5,443,986.

b) Cell Rolling Assays

In a related but alternative aspect, the present invention provides methods, devices and systems for use in performing in vitro cell rolling assays. In particular, it has been reported that several classes of cell adhesion molecules participate in a wide range of important physiological functions, including wound healing, inflammation and cancer metastasis. Some examples of these molecules include selectins and integrins which mediate the rolling and subsequent immobilization of white blood cells along the endothelial lining of blood vessel, thus allowing then to migrate out of the blood vessel and toward the target tissue. Cell rolling assays are designed to mimic in vitro the rolling phenomenon in vivo, to create a more effective model for use in screening potential effectors of that phenomenon. Lawrence et al., J. Immunol., (1993) 151:6338–6346; Brunk et al., Biophys. J. (1997) 72:2820–2833.

Generally, the assay is performed by flowing a suspension of cells over a surface upon which ligands are immobilized, and observing the numbers of firmly attached and/or rolling cells on that surface as well as the velocity of the rolling cells. The present invention employs the microfluidic systems described herein, in the performance of these assay types. In particular, as described in greater detail below, the cell suspension bearing an appropriate reference label, is introduced into a channel in which an appropriate ligand of interest is immobilized on the inner surface. Immobilization of ligands on the interior surface of channels is optionally accomplished by covalently attaching the ligands to the surface or by adsorbing the ligands on the surface. Covalent attachment of ligands to surfaces of solid substrates as been described in the art. See, e.g., Sundberg, et al., J. Am. Chem. Soc. (1995) 117:12050–57.

In accordance with the present invention, the cell suspension is flowed through the channel, i.e., using pressure flow as described in greater detail below, and the number of cells that are rolling over or firmly attached to the interior surface of the channel is monitored using an appropriate detection system. Alternatively, cells are pulsed through the channel to facilitate their monitoring. Typically, such systems employ a video imaging system that images and identifies the cells as they enter the imaged area, and tracks the cells path through the field, determining their relative velocity. Alternatively, point detection systems, e.g., as described herein, are used which detect cells at two separate points in the channel, and determine their relative velocity. In the latter case, it is generally desirable to provide the cells in suspension that is sufficiently dilute so as to permit correlation between the two detectors. Alternatively, cells may be coded with mixtures of different, distinguishable labels to permit the correlation among cells between points. Such coded cells may include wide varieties of different labels, or alternatively, may include a set of two, three, four, five, six, seven or eight different labels at varying relative levels, where the profile of the relative levels of labels identifies the different cells.

Figure 2B:
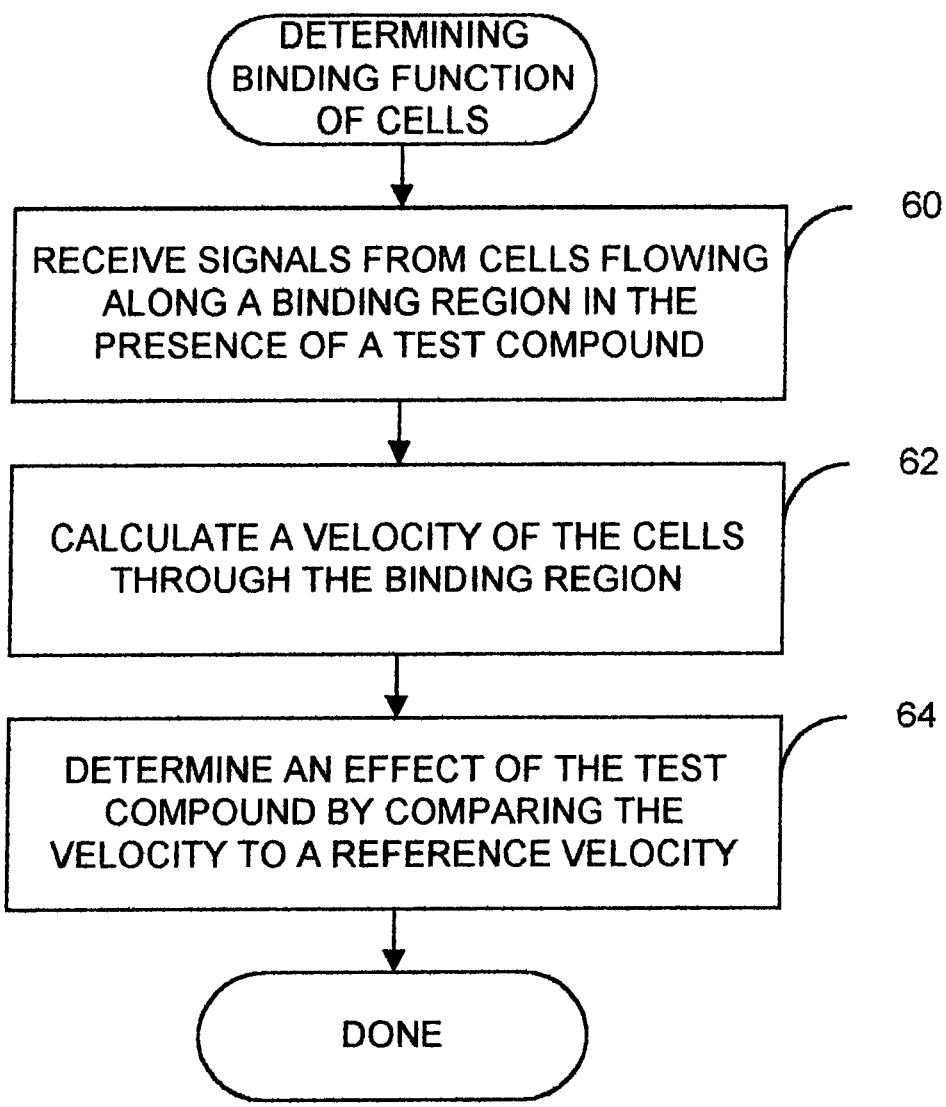

FIG. 2B shows a flowchart of a process of determining the binding function of cells. Typically, the fluid channel has a binding moiety immobilized on an interior surface of the fluid channel and the cells include on their surfaces a moiety bound by the binding moiety. At a step 60, signals from cells in a suspension flowing along the binding region of the fluid channel in the presence of a test compound are received. The signals can correspond to a detectable property of the cells as described herein.

At a step 62, a velocity of the cells through the binding region is calculated by analyzing the signals. For example, a time difference between when the signals indicate the cells passed first and second points on the fluid channel can be determined, where the first and second points are spaced apart along the fluid channel. The velocity of the cells can be calculated from the time difference and the distance along the channel between the first and second points. Thus, the velocity can be calculated by dividing the distance by the time difference.

The effect of the test compound on the binding function of the cells is determined by comparing the velocity to a reference velocity at a step 64. In one embodiment, the reference velocity is of the cells flowing along the binding region of the fluid channel in the absence of the test compound. In another embodiment, the fluid channel includes a non-binding region having substantially no binding moiety immobilized therein. Thus, the reference velocity can be calculated by analyzing signals from cells flowing along the non-binding region of the fluid channel in the presence of the test compound.

The effect of the test compound (or multiple different test compounds) can be displayed to a user. As an example, if the velocity of the cells is less than the reference velocity, the user can be informed that the test compound is an inhibitor of the binding function of the cells. Conversely, if the velocity of the cells is greater than the reference velocity, the user can be informed that the test compound is an enhancer of the binding function of the cells.

In screening assays, the test compounds are introduced into the analysis channel, e.g., via an external sample accessing capillary (i.e., an electrokinetic injector) where they contact the suspension of cells. The cell suspension is then assayed for rolling or firmly attached cells, and the effect of the test compound, if any, on the cell rolling or binding is determined as compared to the control, e.g., in the absence of the test compound.

3. Viability

In still another respect, the methods and systems of the present invention are also particularly applicable in performing cell viability assays, and particularly for screening test compounds for their effects on cell viability. Such assays are generally utilized in performing toxicity studies, antibiotic screening methods, and the like, and are particularly suitable for the methods and systems of the present invention. Accordingly, in these aspects, the cellular function specific indicator is an indicator of cell viability.

In operation, the suspension of cells includes a reference label as described above. The cells are also treated with a second function labeling group that indicates the viability of the cells in the suspension. Specifically, the function label preferentially stains or labels either viable or non-viable cells. A variety of viability indicative dyes are generally commercially available. For example, fluorogenic esterase substrates, such as calcein AM, BCECF AM and fluorescein diacetate, can be loaded into adherent or nonadherent cells, and are suitable indicators of cell viability. Specifically, these esterase substrates measure both esterase activity, which is required to activate the fluorescence of the dye, as well as cell-membrane integrity, which retains the fluorescent materials intracellularly. Other suitable viability indicators include polyfluorinated fluorescein derivatives (i.e., DFFDA, TFFDA, HFFDA and $Br_4TFFDA$), polar nucleic acid based dyes (i.e., SYTOX Green™), dimeric and monomeric cyanine dyes (i.e., TOTO™ and TO-PRO™ series dyes from Molecular Probes), ethidium and propidium dyes (i.e., ethidium bromide, ethidium homodimer and propidium iodide).

Depending upon the viability indicator used, the level of function label is indicative of the number of either viable or non-viable cells, while the level of reference label is indicative of the number of total cells, e.g., viable and non-viable. Comparison of the levels of the two labels then provides an indication of the relative viability of the cells in the suspension, regardless of the number of cells being detected, e.g., multiple cells, aggregates, or individual cells). In particular, where two cell populations show a similar level of reference label, but one population shows a lower level of viability indicator, it will be understood that the second population is less viable, e.g., has more nonviable cells. It will be appreciated that many dyes or labels described for use as reference labels are also often used as viability labels. Accordingly, it will generally be desirable to select a reference label that labels both viable and nonviable cellular material, and which is distinguishable from the function label. Examples of such reference labels include, e.g., lipophilic membrane labels, and the like.

In performing screening assays, cell suspensions that are exposed to different test compounds or agents are flowed past the detection point and the relative viability of the cells is determined, as compared to a control. Increases or decreases in cellular viability indicate that the compound or agent improves or decreases cellular viability. Such assays are readily employed in identifying antimicrobial, antibiotic or other viability affecting agents. Similarly, such assays are optionally employed in screening for effectors of pathways involved in apoptosis or programmed cell death, e.g., ras mediated pathways.

4. Expression

In a further aspect, the methods and systems of the present invention are used to assay cellular expression functions, and particularly, for the effect of test compounds on such cellular expression. Such assays are generally utilized in screening for effectors of given biological processes, which effectors target those functions at the gene expression level. In accordance with the present invention, therefore, the function label is indicative of the level of gene expression, for a particular gene of interest.

Gene expression levels are typically assayed by quantifying the level of gene product from the gene of interest, e.g., the amount of protein produced by the cells. Alternate methods of gene expression analysis examine the amount of RNA transcribed from the gene of interest. Typically, such assays involve the use of a nucleic acid hybridization assay to identify a pattern of RNA transcription following an activating event.

The methods and systems of the present invention are readily applied to such expression analyses. In particular, in accordance with the present invention, the function label is typically provided that is expressed by the cells during the expression function. For example, chimeric reporter systems may be employed as function labels or indicators of gene expression. Chimeric reporter systems typically incorporate a heterogeneous reporter system integrated into the coding sequence of the gene of interest. The expression of the gene of interest is then accompanied by the expression of the reporter, which is then detected. For example, a receptor may be fusion between the product of the gene of interest and heterologous protein, e.g., an enzyme whose activity is readily assayable, or an otherwise detectable protein, e.g., luciferase, aequorin, green fluorescent protein (GFP), -galactosidase, alkaline phosphatase, or the like. The expressed reporter is then detected and compared with the level of reference label, to provide a quantitative determination of expression levels on a per cell basis. Expression of gene products to a detectable level can require varying amounts of time, e.g., several minutes to hours. Accordingly, the assay time is varied to allow such expression. As noted herein, such variation is generally accomplished by one or more of slowing the flow rates of the cell suspension through the analysis channel and/or lengthening the analysis channel.

Alternatively, the function label is provided as an element of a binding molecule that specifically associates with the downstream indicator of gene expression, e.g., an expressed protein, wherein the binding of the binding molecule (bearing the function label) to the gene product of interest produces a detectable property within the cell, e.g., as described with reference to the binding assays, above. The assay methods are then carried out in the same manner as described with reference to the binding functions, described above. In the case of expressed proteins, the binding molecule optionally includes an antibody specific for the gene product, or a specific binding partner, where the expressed protein is a member of a binding pair, e.g., a receptor or ligand.

Because gene expression assays typically require much longer incubation times than other assay types described herein, modified methods are optionally employed. For example, in one aspect, cells are flowed through the channel of the system, and preferably, through multiple parallel channels of the system, and contacted with surfaces of the channel(s) that cause them to adhere. Test compounds are then introduced into the channel(s) and allowed to flow over the adhered cells, e.g., for from 5 to 60 minutes. Any effects of these test compounds on the level of function label, and therefore, gene expression, is determined in the channel(s), and compared to the level of reference label. The comparison then allows quantification of the level of expression on a per cell basis. Optionally, the reaction channel is provided such that the travel time of the cells from the point of test compound addition to detection is sufficient to permit appropriate expression analysis. In certain aspects, tortuous channels, e.g., serpentine channels, and the like, are used to extend channel lengths to expand the travel time. Alternatively or additionally, flow rates are substantially reduced to increase this travel time.

B. Screening Assays

As noted repeatedly above, the assays described herein are particularly useful in performing high-throughput screening assays. As used herein, the term "test compound" refers to the collection of compounds that are to be screened for their ability to affect a particular biochemical system. Test compounds may include a wide variety of different compounds, including chemical compounds, mixtures of chemical compounds, e.g., polysaccharides, small organic or inorganic molecules, biological macromolecules, e.g., peptides, proteins, nucleic acids, or an extract made from biological materials such as bacteria, plants, fungi, or animal cells or tissues, naturally occurring or synthetic compositions. Depending upon the particular embodiment being practiced, the test compounds may be provided, e.g., injected, free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, glass beads, polyaminemethylvinylether maleic acid copolymer, amino acid copolymer, ethylene-maleic acid copolymer, nylon, silk, etc. Additionally, for the methods and apparatuses described herein, test compounds may be screened individually, or in groups. Group screening is particularly useful where hit rates for effective test compounds are expected to be low such that one would not expect more than one positive result for a given group. Alternatively, such group screening may be used where the effects of different test compounds may be differentially detected in a single system, e.g., through electrophoretic separation of the effects, or differential labeling which enables separate detection.

Typically, vast libraries of test compounds are separately tested for potential effects on different cellular functions In preferred aspects, large libraries of chemical compounds prepared using combinatorial synthesis techniques are typically employed as test compounds in high-throughput screening applications, to identify any such compounds that may have pharmacologically beneficial activities. In optional preferred aspects, test compounds can include large libraries of naturally occurring materials or compounds, libraries of genetic material, protein fragments, and the like.

In general, the test compounds are separately introduced into the assay systems described herein. The relative level of a particular cellular function is then assessed in the presence of the test compound, and this relative level of function is then compared to a control system, which lacks an introduced test compound. Increases or decreases in relative cellular function are indicative that the test compound is an enhancer or an inhibitor of the particular cellular function, respectively.

III. Assay Systems

A. Overall Systems

Figure 3:
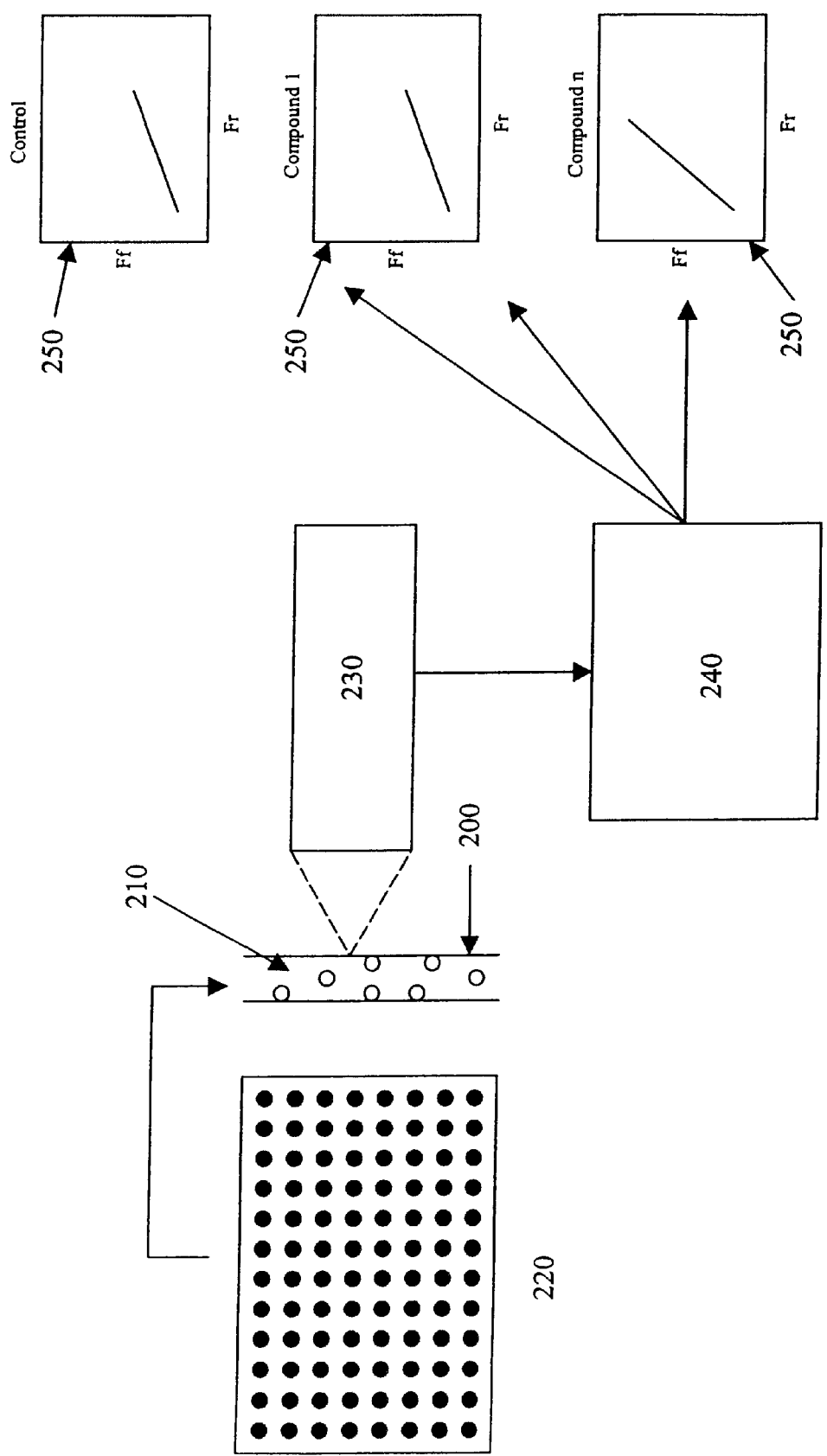
FIG. 3 is a schematic illustration of an overall system for carrying out the assay and screening methods of the invention.

As noted above, the present invention also provides systems and devices used to practice the above-described methods. A schematic illustration of a system for carrying out these assay methods is illustrated in FIG. 3. As shown, the system includes a fluidic channel 200 along which is flowed a suspension of cells 210 that bear a reference label and a function label. A source of different test compounds 220 is optionally linked to the channel 200, for introducing the different test compounds into the channel whereupon they are contacted with the cells. One or more detectors 230 are also provided in sensory communication with the channel 200, for detecting and quantifying both the level of reference label and the level of function label present on the cells. As used herein, the phrase "sensory communication" refers to orientation of the detector such that it is capable of obtaining an appropriate signal from the point of interest. In the case of optical detectors, sensory communication provides a detector oriented such that it is capable of receiving an optical signal from a channel of a microfluidic device. Such detection may be direct, or may include an intervening optical pathway, e.g., lenses, fiber optics, etc. In the case of chemical detectors, such sensory communication typically requires a sensor component disposed in contact with the fluid material within the channel.

The detector(s) is operably linked to a computer 240, e.g., a computer for recording the detected levels of reference and function labels, for comparing the level of function label to the level of reference label, and for providing a report of relative activity of the cells that are being assayed 250. The computer 240 also typically includes appropriate programming for determining whether one assay, e.g., a first screening assay, shows greater or lesser cellular function than another assay, e.g., a control.

Figure 4:
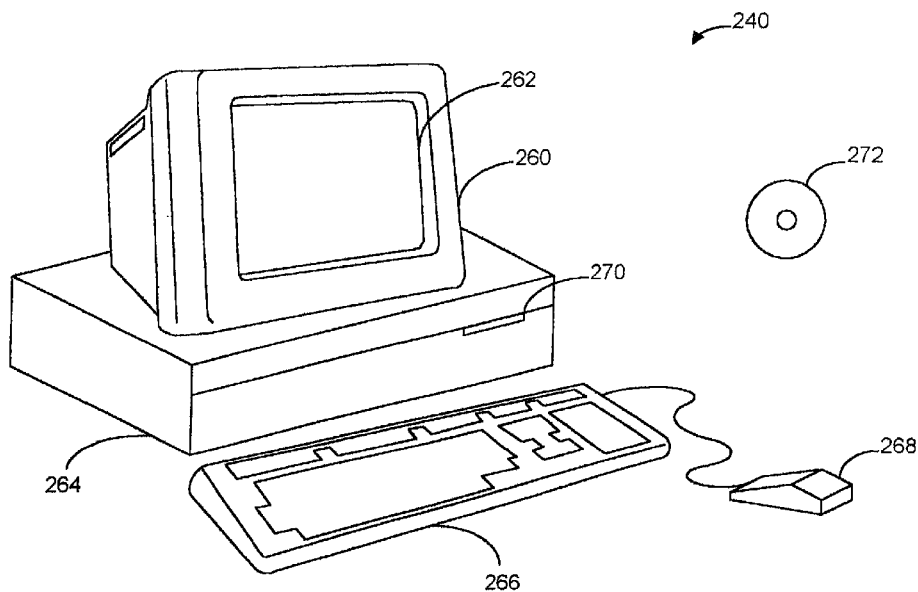
FIG. 4 illustrates an example of a computer system that may be utilized to execute the software of an embodiment of the invention.

FIG. 4 illustrates an example of a computer system that can be used to execute the software of an embodiment of the invention. FIG. 4 shows computer system 240 that includes a display 260, screen 262, cabinet 264, keyboard 266, and mouse 268. Mouse 268 can have one or more buttons for interacting with a graphical user interface. Cabinet 264 houses a CD-ROM drive 270, system memory and a hard drive (see FIG. 5) which can be utilized to store and retrieve software programs incorporating computer code that implements the invention, data for use with the invention, and the like. Although a CD-ROM 272 is shown as an exemplary computer readable storage medium, other computer readable storage media including floppy disk, tape, flash memory, system memory, and hard drive can be utilized. Additionally, a data signal embodied in a carrier wave (e.g., in a network including the Internet) can be the computer readable storage medium.

Figure 5:
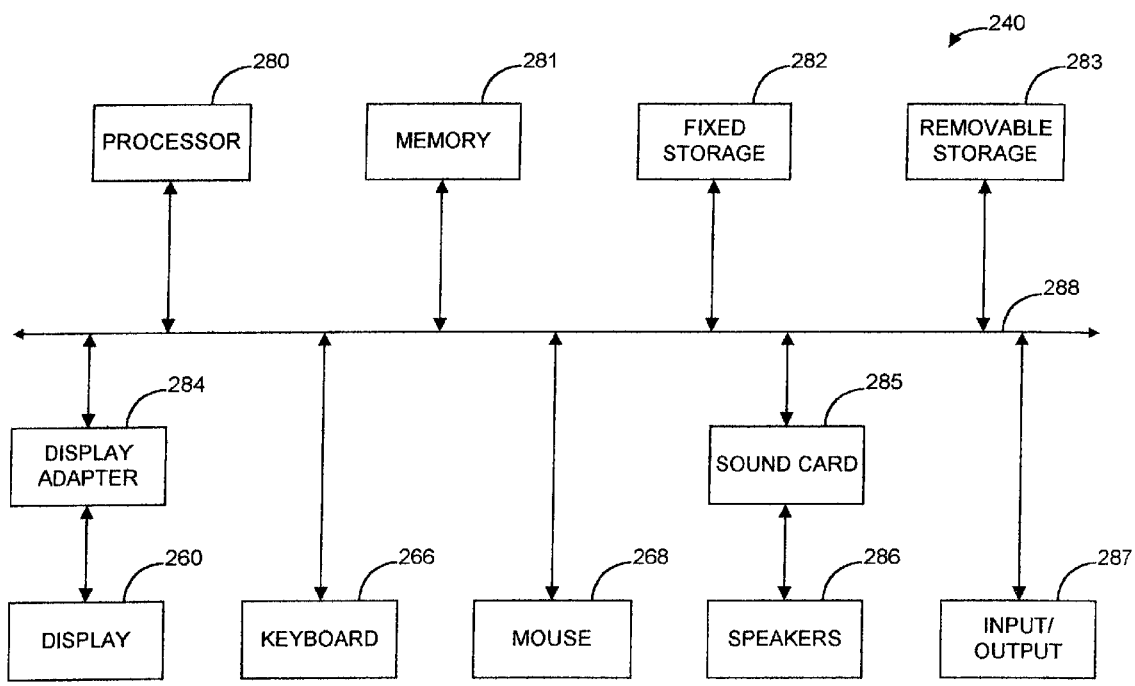
FIG. 5 illustrates a system block diagram of the computer system of FIG. 3.

FIG. 5 shows a system block diagram of computer system 240 used to execute the software of an embodiment of the invention. As in FIG. 4, computer system 240 includes display 260, keyboard 266 and mouse 268. Computer system 240 further includes subsystems such as a central processor 280, system memory 281, fixed storage 282 (e.g., hard drive), removable storage 283 (e.g., CD-ROM drive), display adapter 284, sound card 285, speakers 286, and input/output interface 287. Input/output interface 287 can be a serial, parallel or other interface for communication with other devices, such as for fluidics and/or detection. Other computer systems suitable for use with the invention can include additional or fewer subsystems. For example, another computer system could include more than one processor 280 (i.e., a multi-processor system) or a cache memory.

The system bus architecture of computer system 240 is represented by arrows 288. However, these arrows are illustrative of any interconnection scheme serving to link the subsystems. For example, a local bus could be utilized to connect the central processor to the system memory and display adapter. Computer system 240 shown in FIG. 5 is but an example of a computer system suitable for use with the invention. Other computer architectures having different configurations of subsystems can also be utilized.

Computer system 240 can be in electronic communication with apparatuses for introducing fluids and compounds into a microfluidic device, for causing cells to flow through the microfluidic device and for measuring the presence of cells (such as by a detector) at a detection point. Such a computer system can perform the data analysis in real time. However, data analysis can also be performed in real time (or in batch mode) by sending signals to a computer system for analysis. For example, computer system 240 can receive signals over a wide area network and perform data analysis at a remote location.

Figure 6:
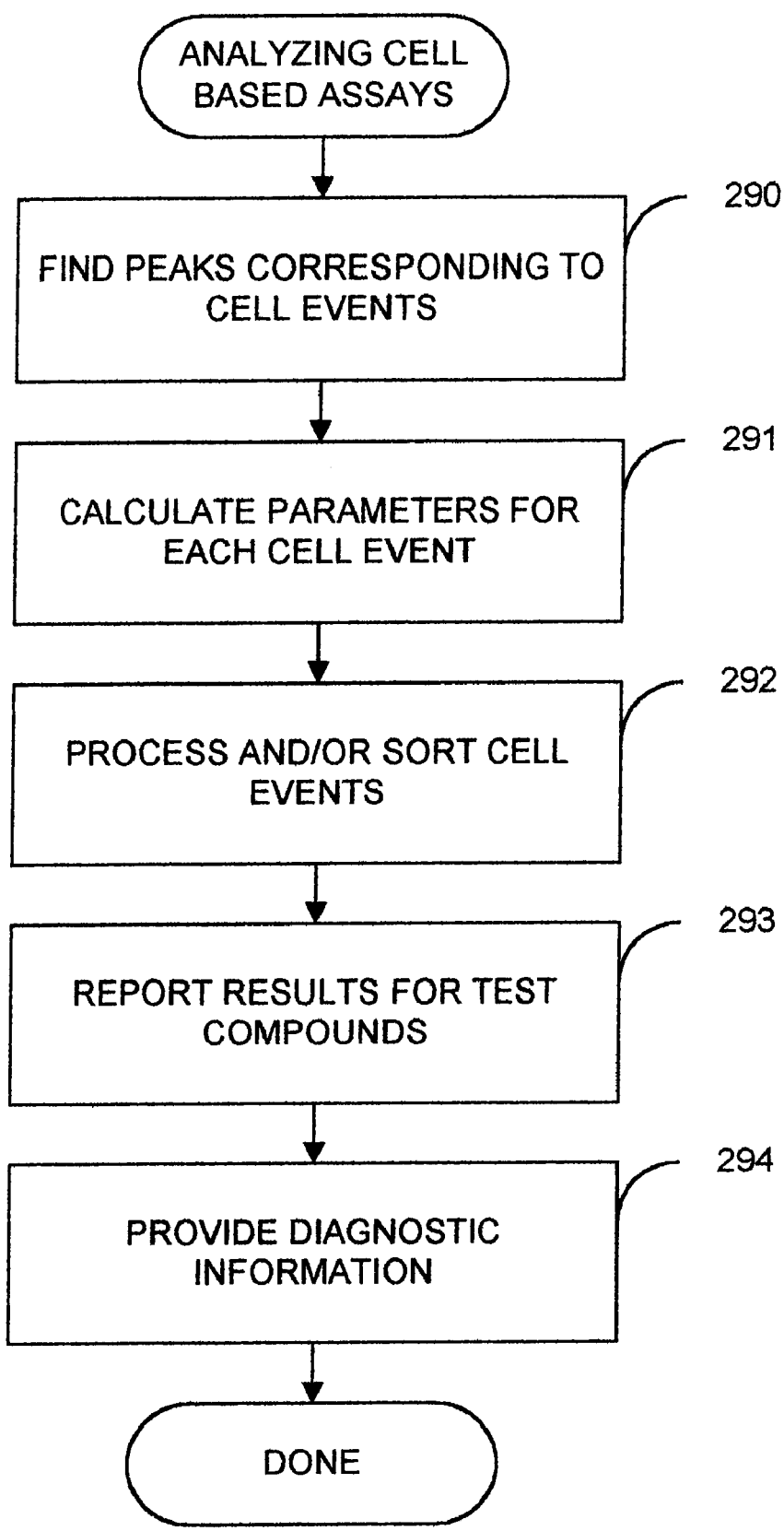
FIG. 6 shows a flowchart of a process of analyzing cell based assays.

FIGS. 2A and 2B showed flowcharts for processing data from cell events but it may be beneficial to discuss an example of an overall process of analyzing cell based assays. FIG. 6 shows a flowchart of a process of analyzing cell based assays for discreet cell events. At a step 290, peaks corresponding to cell events are found. In one embodiment, the data includes fluorescence from two channels: channel A and channel B. In general, a cell event can be defined as the presence of a peak in the fluorescence data for channel A, channel B, channel A and B, or channel A or B. Typically, the ratio of peak heights to baseline noise is greater that 10 but it may be as low as 3 or 4. Cell fluorescence peaks can include 1–5 data points (or more) and the average number of data points between cells can be between 3 and 20. Although two fluorescence channels can be utilized, embodiments of the invention can use other types of labels and fewer or more channels. In some embodiments, the user is able to adjust parameters to optimize cell identification.

At a step 291, parameters are calculated for each event. Examples of parameters include the peak height for each channel, the peak area for each channel, the ratio of peak heights, and the ratio of peak areas. Additionally, logic can be specified to determine parameters. For example, if channel C<threshold, the ratio calculated is A/B, but if channel C>threshold, the ratio calculated is B/A.

Cell events are processed and/or sorted at a step 292. Cell events can be processed as described in reference to FIGS. 2A and 2B. Additional processing can also be performed. For example, "dead" cells can be removed from further analysis, where dead cells are defined by in terms of one or more parameters for a cell (e.g., a cell is "dead" if channel B>threshold1 and A/B<threshold2). Additionally, cells can be grouped for separate analysis based on one or more parameter. Thus, cell events with high fluorescence in channel B can be classified as one cell type and analyzed separately from cells with low fluorescence in channel B. The significance of the various parameters can preferably be defined and changed by the user.

At a step 293, results for test compounds are reported, such as by being displayed to a user. Additionally, the user should be able to view data such as the average, standard error of the mean and population distributions (e.g., histograms) for all cells in contact with the test compounds. In order to support research and development activities, the analysis in some embodiments is able to proceed in the absence of dye peaks by allowing the user to group cells by user specified time windows.

Additionally, the user is able to adjust reported cell parameters based on user selected samples. For example, the user may decide to normalize all the data from one plate using positive and negative controls found on that plate. As another example, the cell parameters may be adjusted based on assay dependent information. As yet another example, the peaks in channel B can be corrected for dye leakage by correcting for long term drift in the average peak height in channel B.

At a step 294, diagnostic information is provided. As a screening run may take many hours, a user may find it beneficial to look at trends in the baseline for each channel, trends in the peak height and/or peak are for each channel and trends in the peak height ratio or peak area ratio. Additionally, trends such as the number of cell events recorded per unit time, the number of data points per cell event, time between dye peaks and dispersion of dye peaks (e.g., peak height, peak width at half max and peak width at 10% of max) can be made available to the user. These trends can be very helpful in diagnosing the assays.

Figure 10:
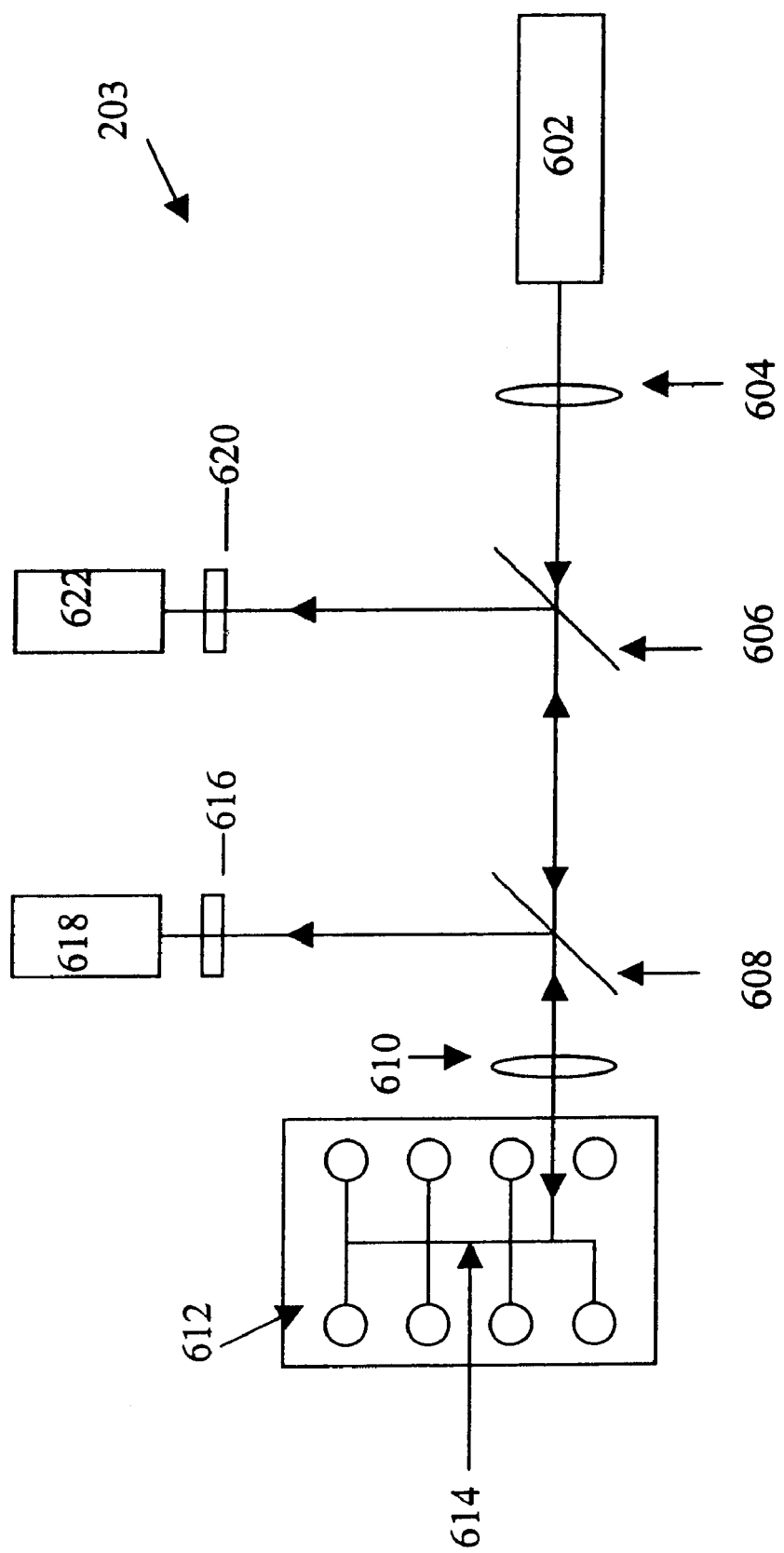
FIG. 10 is a schematic illustration of an optical detection system for separately detecting reference and function labels from cell suspensions.

Returning to FIG. 3, detector 230 optionally includes one or more different detectors, and is selected to detect both the reference and function labels present in the cells. For example, in the case of cells that include reference and function labels that are fluorescent, the detector typically includes a dual wavelength fluorescent detector. A schematic illustration of such a detector is shown in FIG. 10. As shown, the detector 230 includes a light source 602. Appropriate light sources may vary depending upon the type of detection being employed. For example, in some cases broad spectrum illumination is desirable while in other cases, a more narrow spectrum illumination is desired. Typically, the light source is a coherent light source, such as a laser, or laser diode, although other light sources, such as LEDs, lamps or other available light sources are also optionally employed. In the case of a fluorescent detector, excitation light, e.g., light of appropriate wavelength to excite both reference and function labels, from the light source 602 is directed at the analysis channel 614, e.g., disposed in microfluidic device 612, via an optical train that includes optional lens 604, beam splitters 606 and 608 and objective lens 610. Upon excitation of both the reference and function labels present in channel 614, e.g., associated with cells in the channel, the emitted fluorescence is gathered through the objective lens 610 and passed through beam splitter 608. A portion of the emitted fluorescence is passed through a narrow band pass filter 616 which passes light having a wavelength approximately equal to the excitation maximum (the emitted fluorescence) of one of the two labels, while filtering out the other label's fluorescence, as well as any background excitation light. Another portion of the emitted fluorescence is passed onto beam splitter 606 which directs the fluorescence through narrow band pass filter 620, which passes light having the wavelength approximately equal to the emission maximum of the other label group. One or more of beam splitters 608 and 606 are optionally substituted with dichroic mirrors for separating the label fluorescence and/or any reflected excitation light. Detectors 618 and 622 are typically operably coupled to a computer that records the level of detected light as a function of time from the beginning of the assay.

As described in greater detail herein, in some instances, electrokinetic material transport systems are used to direct one or more of the flow of cell suspensions, the injection of test compounds, and other material movement parameters. In such cases, the overall system used in performing the assay will typically include an appropriate controller and interface for controlling such electrokinetic material transport. Typically, such transport systems include one or more electrical power supplies that are operably coupled to the termini of the channels in a microfluidic device, e.g., as described in greater detail below. The connection of the power supply(ies) with the channels is typically accomplished via electrodes placed into reservoirs at the termini of the channels, which electrodes are coupled to the power supply(ies). The power supply(ies) then delivers appropriate voltage levels to the various electrodes to yield a desired flow pattern within the channels of the device, e.g., flowing the cell suspension and periodically injecting a test compound. The power supply is typically linked to an appropriately programmed computer which directs the application of voltages in accordance with a user selected flow profile.

B. Assay Devices

As noted above, the assays of the present invention are carried out within fluidic channels, along which the cell suspensions are flowed. In some cases, the channels may simply be present in a capillary tube, e.g., a glass, fused silica, quartz or plastic capillary. The capillary channel is fluidly coupled to a source of the suspension of cells, which are then flowed along the capillary channel. In particularly preferred aspects, the channel is integrated into the body structure of a microfluidic device. As used herein, the term "microfluidic" generally refers to one or more fluid passages, chambers or conduits which have at least one internal cross-sectional dimension, e.g., depth, width, length, diameter, etc., that is less than 500 $\mu$m, and typically between about 0.1 $\mu$m and about 500 $\mu$m.

In the devices of the present invention, the microscale channels or chambers preferably have at least one cross-sectional dimension between about 0.1 $\mu$m and 200 $\mu$m, more preferably between about 0.1 $\mu$m and 100 $\mu$m, and often between about 0.1 $\mu$m and 50 $\mu$m. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication.

The body structure of the microfluidic devices described herein typically comprises an aggregation of two or more separate layers which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device.

Figure 7:
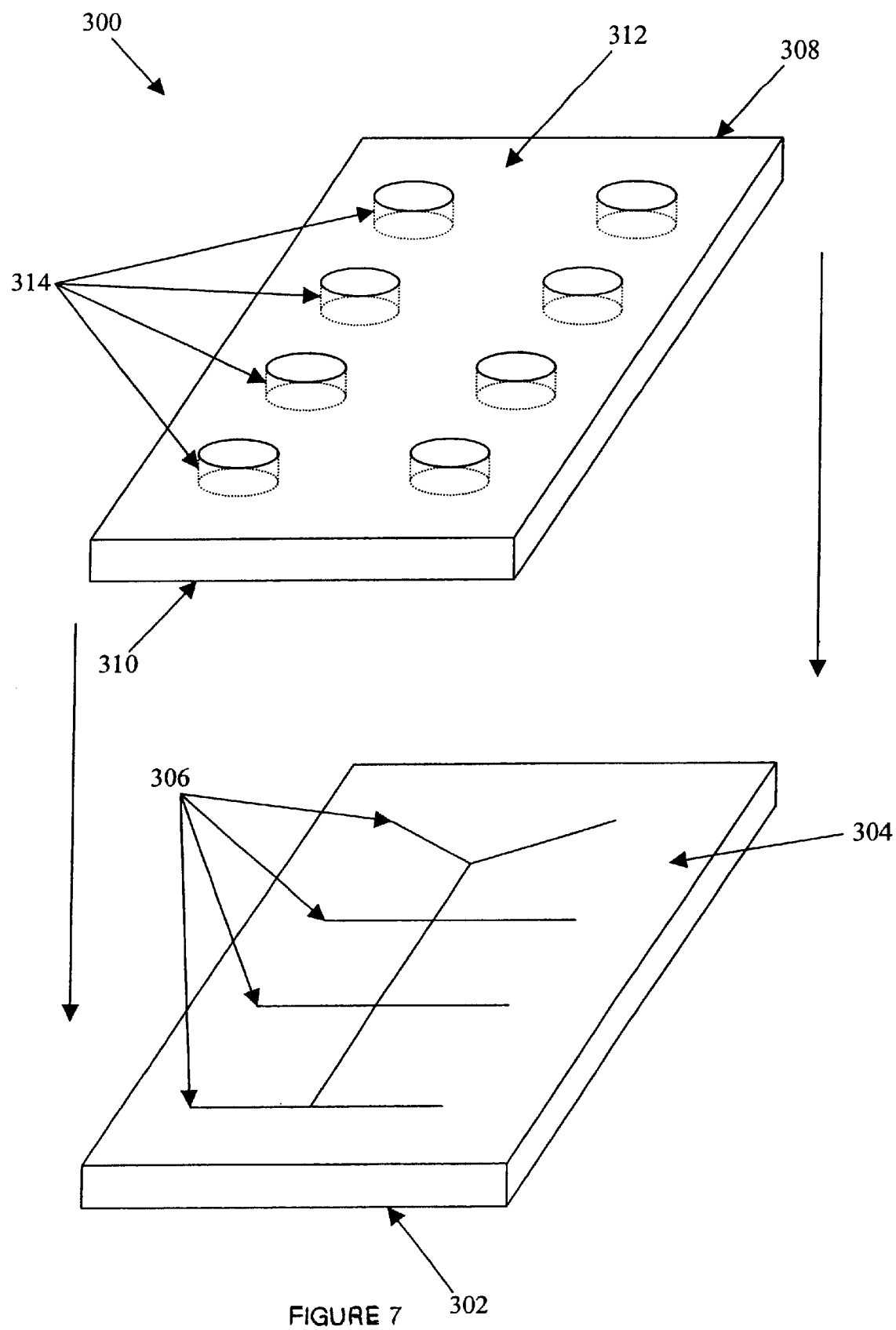
FIG. 7 is a schematic illustration of a microfluidic device incorporating a layered body structure.

FIG. 7 illustrates a two-layer body structure 300, for a microfluidic device. In preferred aspects, the bottom portion of the device 302 comprises a solid substrate that is substantially planar in structure, and which has at least one substantially flat upper surface 304. A variety of substrate materials may be employed as the bottom portion. Typically, because the devices are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (See U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. patent application Ser. No. 08/843,212, filed Apr. 14, 1997, and which is incorporated herein by reference in its entirety for all purposes.

The channels and/or chambers of the microfluidic devices are typically fabricated into the upper surface 304 of the bottom substrate or portion 302, as microscale grooves or indentations 306, using the above described microfabrication techniques. The top portion or substrate 308 also comprises a first planar surface 310, and a second surface 312 opposite the first planar surface 310. In the microfluidic devices prepared in accordance with certain aspects of the methods described herein, the top portion 308 also includes a plurality of apertures, holes or ports 314 disposed therethrough, e.g., from the first planar surface 310 to the second surface 312 opposite the first planar surface.

The first planar surface 310 of the top substrate 308 is then mated, e.g., placed into contact with, and bonded to the planar surface 304 of the bottom substrate 302, covering and sealing the grooves and/or indentations 306 in the surface of the bottom substrate, to form the channels and/or chambers (i.e., the interior portion) of the device at the interface of these two components. Bonding of substrates is typically carried out by any of a number of different methods, e.g., thermal bonding, solvent bonding, ultrasonic welding, and the like.

The holes 304 in the top portion of the device are oriented such that they are in communication with at least one of the channels and/or chambers formed in the interior portion of the device from the grooves or indentations in the bottom substrate. In the completed device, these holes function as reservoirs for facilitating fluid or material introduction into the channels or chambers of the interior portion of the device, as well as providing ports at which electrodes may be placed into contact with fluids within the device, allowing application of electric fields along the channels of the device to control and direct fluid transport within the device. In many embodiments, extensions are provided over these reservoirs to allow for increased fluid volumes, permitting longer running assays, and better controlling fluid flow parameters, e.g., hydrostatic pressures. Examples of methods and apparatuses for providing such extensions are described in U.S. application Ser. No. 09/028,965, filed Feb. 24, 1998, and incorporated herein by reference.

In many embodiments, the microfluidic devices will include an optical detection window disposed across one or more channels and/or chambers of the device. Optical detection windows are typically transparent such that they are capable of transmitting an optical signal from the channel/chamber over which they are disposed. Optical detection windows may merely be a region of a transparent cover layer, e.g., where the cover layer is glass or quartz, or a transparent polymer material, e.g., PMMA, polycarbonate, etc. Alternatively, where opaque substrates are used in manufacturing the devices, transparent detection windows fabricated from the above materials may be separately manufactured into the device.

In many aspects, it is desirable to provide the interior surfaces of the channels with an appropriate treatment to prevent the adhesion of cells to that surface. For example, in the case of glass or other highly charged channel surfaces, some cell types may have a tendency to stick to the channel surfaces, interfering with the flowing of cells through the channels. For example, in the case of mammalian cell based assays, many mammalian cell types are particularly adherent to certain types of surfaces, e.g., glass and some plastics. Accordingly, in some embodiments, it is desirable to treat or coat the interior surfaces of the channels to prevent cell adhesion. A variety of surface treatments are optionally employed to accomplish this goal. For example, charge masking coatings such as polyols (e.g., polyvinylalcohol (PVA)) polyethyleneimine (PEI), polyethylene glycol (PEG), polyacrylamides (e.g., polyacrylamide, polymethylacryalamide, polydimethacrylamide, and the like), carbohydrates such as polysucrose (ficoll), polyglucose (dextran and cellulose), and polytetrafluoroethylene (Teflon™), etc.. Alternatively, covalent surface treatments are also optionally used to prevent surface adhesion of cells, such as silanization (e.g., using dimethyl or dichlorosilane) of glass or plastic surfaces. Other surface treatments are generally described above, with reference to device fabrication techniques, above.

The flowing of the suspension of cells along the analysis channels of the devices described herein is optionally carried out by a number of mechanisms, including pressure based flow, electrokinetic flow, or mechanisms that utilize a hybrid of the two. In a first preferred aspect, a pressure differential is used to flow the suspension of cells along the analysis channel. Application of a pressure differential along the analysis channel is carried out by a number of means. For example, in a simple passive aspect, the cell suspension is deposited in a reservoir at one end of the analysis channel and at a sufficient volume or depth, that the cell suspension creates a hydrostatic pressure differential along the length of the analysis channel, e.g., by virtue of its having greater depth than a reservoir at an opposite terminus of the channel. The hydrostatic pressure then causes the cell suspension to flow along the length of the channel. Typically, the reservoir volume is quite large in comparison to the volume or flow through rate of the channel, e.g., 10 $\mu$l reservoirs, vs. 1000 $\mu m^2$ channel cross-section. As such, over the time course of the assay, the flow rate of the cell suspension will remain substantially constant, as the volume of the reservoir, and thus, the hydrostatic pressure changes very slowly. Applied pressure is then readily varied to yield different cell suspension flow rates through the channel. In screening applications, varying the flow rate of the cell suspension is optionally used to vary the incubation time of the cells with the test compound. In particular, by slowing the cells flow rate along the channel, one can effectively lengthen the amount of time between introduction of test compounds and detection of their effects. Alternatively, analysis channel lengths, detection points, or test compound introduction points are varied in fabrication of the devices, to vary incubation times.

In many applications, it may be desirable to provide relatively precise control of the flow rate of the cell suspension, e.g., to precisely control incubation times, etc. As such, in many preferred aspects, flow systems that are more active than hydrostatic pressure driven systems are employed. For example, the cell suspension may be flowed by applying a pressure differential across the length of the analysis channel. For example, a pressure source is applied at the cell suspension reservoir at one end of the analysis channel, and the applied pressure forces the suspension through the channel. The pressure source can be pneumatic, e.g., a pressurized gas, or alternatively can be a positive displacement mechanism, i.e., a plunger fitted into a cell suspension reservoir, for forcing the cell suspension through the analysis channel. Alternatively, a vacuum source is applied to a reservoir at the opposite end of the channel to draw the suspension through the channel. Pressure or vacuum sources may be supplied external to the device or system, e.g., external vacuum or pressure pumps sealably fitted to the inlet or outlet of the analysis channel, or they may be internal to the device, e.g., microfabricated pumps integrated into the device and operably linked to the analysis channel. Examples of microfabricated pumps have been widely described in the art. See, e.g., published International Application No. WO 97/02357.

In alternate aspects, other flow systems are employed in transporting the cellular suspension through the analysis channel. One example of such alternate methods employs electrokinetic forces to transport the cells. Electrokinetic transport systems typically utilize electric fields applied along the length of channels that have a surface potential or charge associated therewith. When fluid is introduced into the channel, the charged groups on the inner surface of the channel ionize, creating locally concentrated levels of ions near the fluid surface interface. Under an electric field, this charged sheath migrates toward the cathode or anode (depending upon whether the sheath comprises positive or negative ions) and pulls the encompassed fluid along with it, resulting in bulk fluid flow. This flow of fluid is generally termed electroosmotic flow. Where the fluid includes a cell suspension, the cells are also pulled along. A more detailed description of controlled electrokinetic material transport systems in microfluidic systems is described in published International Patent Application No. WO 96/04547, which is incorporated herein by reference.

In accordance with the methods and systems of the present invention, a voltage gradient is applied along the length of the analysis channel, which includes an inner surface that comprises a surface potential. In the case of glass channels, the surface typically comprises hydroxyl groups. In aqueous systems, e.g., in the presence of the suspension of cells, these hydroxyl groups deprotonate creating a sheath of positive ions in the fluid near the fluid/surface interface. The voltage gradient is typically applied by placing an electrode at different ends of the analysis channel, e.g., in the reservoirs at the termini of the analysis channel. A voltage difference is then applied between the two electrodes, to cause the suspension of cells to electroosmotically flow along the length of the channel, toward the lower potential.

Flow rates are typically varied by increasing or decreasing the voltage gradient along the channel. As described in greater detail below, electrokinetic transport is optionally used to inject test compounds into the flowing cell suspension.

In many instances, a completely electrokinetic transport system is not ideal for use in transporting cell suspensions. In particular, in many cases, the elevated electric fields used in electrokinetic transport can result in permeation of the cells' membranes, e.g., electroporation. Such electroporation of cells can lead to reduced viability of cells, or at the very least, a leaking of cellular contents including reference label. Accordingly, electrokinetic transport systems are optionally used which do not expose the cell suspension to the electric field, which drives the flowing suspension of cells. In particular, and as described in greater detail below with reference to FIG. 9, the devices and systems of the invention optionally employ electroosmotic pressure pumps that utilize an electric field away from the flowing suspension of cells, to drive the flow of the suspension of cells. Electroosmotic pressure pumps are generally described in U.S. application Ser. No. 08/937,958, filed Sep. 25, 1997, which is incorporated herein by reference.

In alternative aspects, flow of the cell suspension is driven by inertial forces. In particular, the analysis channel is optionally disposed in a substrate that has the conformation of a rotor, with the analysis channel extending radially outward from the center of the rotor. The cell suspension is deposited in a reservoir that is located at the interior portion of the rotor and is fluidly connected to the channel. During rotation of the rotor, the centripetal force on the cell suspension forces the cell suspension through the analysis channel, outward toward the edge of the rotor. Multiple analysis channels are optionally provided in the rotor to perform multiple different analyses. Detection of the function and reference labels is then carried out by placing a detector under the spinning rotor and detecting the signal as the analysis channel passes over the detector. Examples of rotor systems have been previously described for performing a number of different assay types. See, e.g., Published International Application No. WO 95/02189. Test compound reservoirs are optionally provided in the rotor, in fluid communication with the analysis channel, such that the rotation of the rotor also forces the test compounds into the analysis channel.

Figure 8:
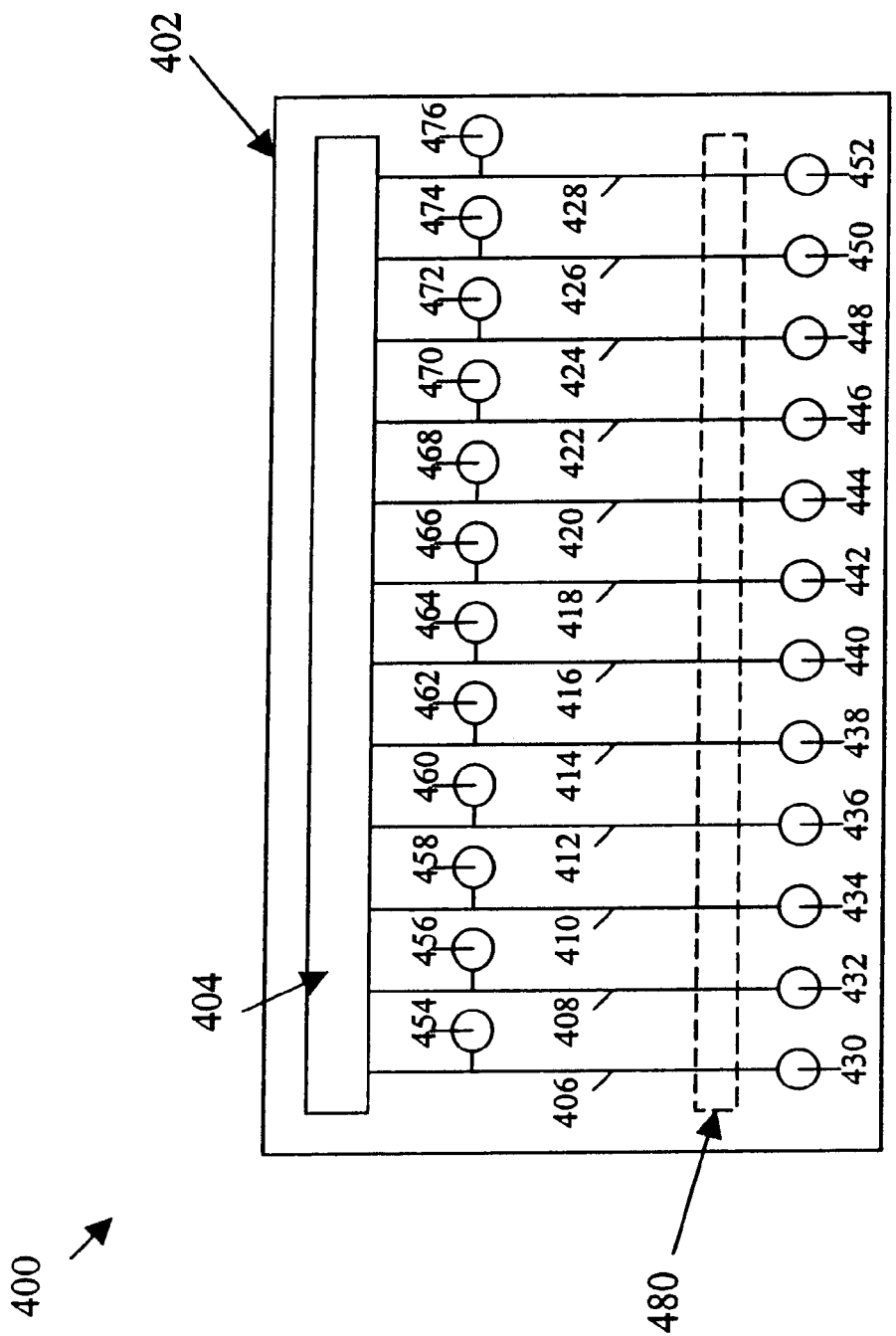
FIG. 8 is a simplified schematic illustration of a microfluidic device for screening multiple test compounds for effects on cells in accordance with the assay methods of the present invention.

A simplified example of a device used in practicing the assay and screening methods described herein, is schematically illustrated in FIG. 8. As shown, the device 400 adopts a planar body structure 402 that was described with reference to FIG. 7, above. The device 400 includes a first reservoir 404 disposed in the body structure 402, and into which the suspension of cells is placed. A plurality of channels 406–428 are provided in the body structure in fluid communication with the cell suspension reservoir 404. As shown, each channel has one terminus in fluid communication with reservoir 404, and the other terminus in communication with a separate reservoir 430–452, respectively. Separate reservoirs for each channel are optional, and are readily replaced with a single receiving or waste reservoir, similar to cell suspension reservoir 404. A source of test compound 454–476 is optionally provided in fluid communication with each separate analysis channel. In operation, the cell suspension is deposited in reservoir 404 and permitted or caused to flow along each of the analysis channels 406–428, and past detection window 480, by one of the flow means described herein, e.g., pressure flow, electrokinetic flow, inertial flow, etc.

Test compounds are placed into the test compound reservoirs 454–476, and permitted or caused to flow into their respective analysis channels. Again, these test compounds may be allowed to flow passively into their respective analysis channels, or may be actively injected, e.g., through pressure or electrokinetic flow means. As the cell suspension passes the detection window 480, the amount of reference and function label is detected in each channel, by one or multiple detectors disposed adjacent to the detection window. Such detectors may include scanning fluorescent detectors that scan across the full length of the detection window, covering several analysis channels in relatively short times, i.e., galvanometer scanners, track scanners and the like. Optionally, linear array scanners are used in the detection process, i.e., incorporating linear arrays of CCDs.

In the performance of cell rolling assays, it will be appreciated that a portion of all or most of the analysis channels 406–428 are optionally provided with one or more different ligands immobilized therein, to assay for cell rolling or firm adhesion. For example, the portion of the channels observed through the detection window 480 typically will include the ligand coated surface.

Figure 9:
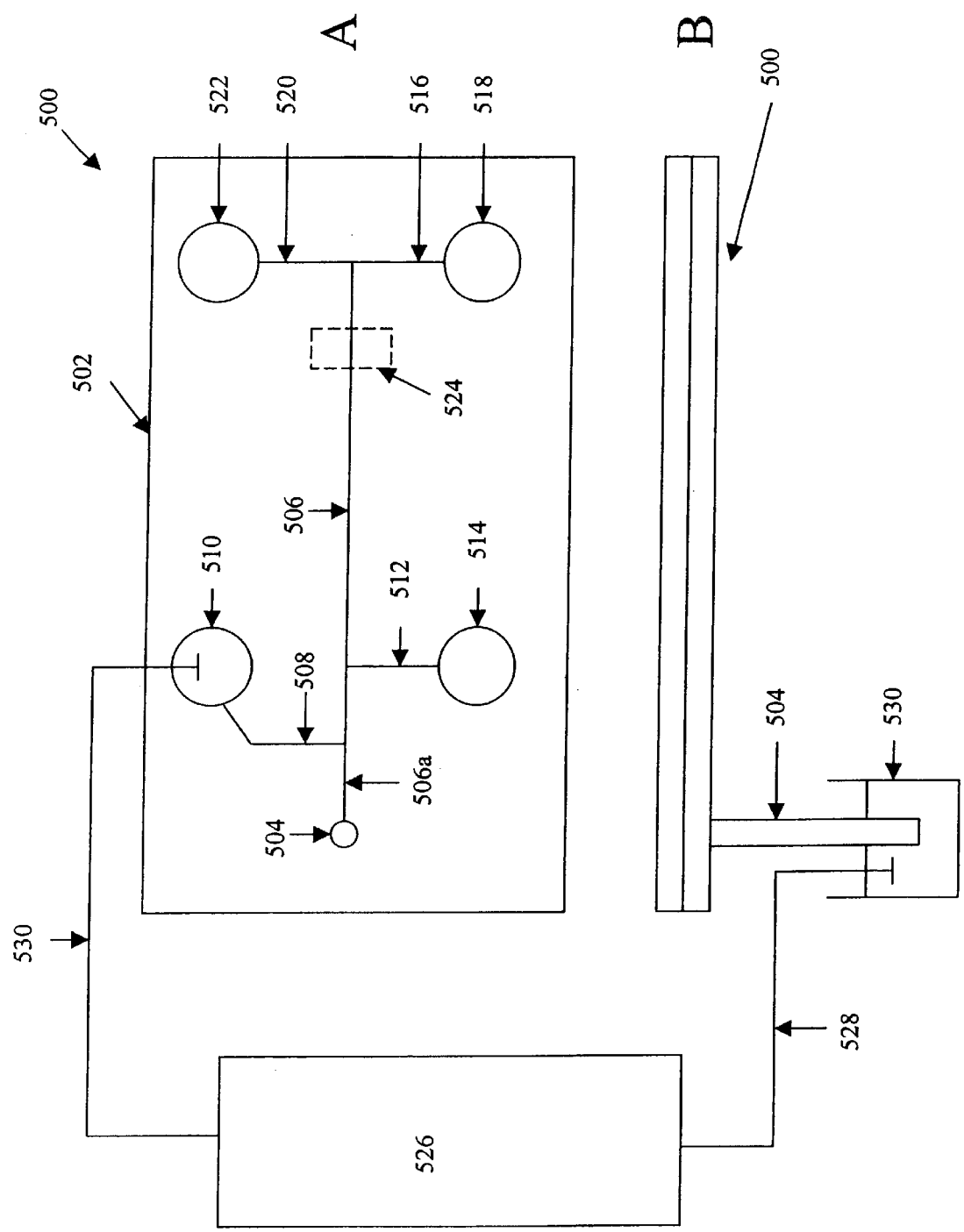
FIG. 9 is a schematic illustration of an integrated system for accessing and screening large numbers of test compounds against cellular systems in accordance with the methods of the present invention.

An alternative example of a device is schematically illustrated in FIG. 9, from a top and side view (panels A and B, respectively). As shown, the device 500 includes an analysis channel 506 disposed in a body structure 502. The analysis channel 506 includes a detection point or window 524 disposed over the analysis channel 506. Typically, the body structure is fabricated from transparent material. As such, the detection point or window can be located over the analysis channel at virtually any point along that channel, depending upon the assay that is to be performed, the amount of incubation time desired, etc. A reservoir 514 is also provided disposed in the substrate, into which is placed a suspension of cells. The cell suspension reservoir 514 is in fluid communication with the analysis channel 506 that is also disposed in the body structure. The reservoir may be directly connected to the analysis channel or it may be connected through an additional channel, e.g., channel portion 512. The device also includes an external sample accessing capillary 504, through which different test compounds are introduced into the analysis channel. Examples of accessing capillaries that are particularly suitable for incorporation into devices of the type shown are electropipettors, e.g., as described in commonly owned published International Patent Application No. 98/00705, which is incorporated herein by reference. Typically, these electropipettors comprise capillary channels that have electrodes disposed at or proximal to their external terminus (the capillary terminus not coupled to the integrated channel network), such that the electrode is in contact with a source of sample or test compound while the end of the capillary is immersed in the sample material. An electric field is then generated between the external electrode and an electrode in communication with the integrated channel structure of the device to electrokinetically drive materials through the capillary into the channel network of the device. These external sample accessing capillaries are then placed in fluid communication with different test compound or sample sources, e.g., different wells in a multiwell plate, by moving the capillary end into each of the wells or sources. This ability to move from sample source to sample source, sipping small amounts of sample allows the capillary to be in "selective fluid communication" with each of the sample sources.

In operation, a suspension of cells is placed into reservoir 514, and the suspension flows into the analysis channel via channel 512. Flowing of the suspension of cells from the suspension reservoir 514, into the analysis channel 506, past the detection window 524, and into the waste reservoir 518, is carried out by any of the flow systems described above, e.g., electrokinetic, pressure based, or the like. As shown, the hydrostatic pressure of the cell suspension in the reservoir 510 is used to flow the cell suspension into the analysis channel 506.

Different test compounds are then obtained from libraries of compounds, e.g., disposed in multiwell plates, e.g., well 530, and introduced into the analysis channel by immersing the sample accessing capillary into the different compound sources or wells and drawing an aliquot of the test compound into the capillary. The aliquot of test compound is subsequently moved into the analysis channel, where it is mixed with the suspension of cells, and the effect of the test compound on the cells, if any, is measured at the detection point.

As noted above, in certain aspects, it may be desirable to avoid subjecting the suspension of cells to electric fields required for electrokinetically transporting the cells. Similarly, electric fields required for introducing test compounds through, e.g., an electropipettor may also have detrimental effects on the cells, in the system. Accordingly, in certain aspects, the electropipettor is configured to function as an electroosmotically driven micropump, for mixing test compounds with cells, and for flowing the cells along the analysis channel.

In such cases, the device shown in FIG. 9 is readily adapted to such flow systems. In particular, in the device 500 illustrated in FIG. 9, electrokinetic introduction of test compounds is accomplished by providing a voltage gradient between the source of test compounds, e.g., fluid well 530, and the integrated channel structure in the interior of the device 500. As shown, the voltage gradient is applied between the fluid well 530 and reservoir 510, such that the test compound is flowed from well 502 into the capillary 504 and into channel portion 506a. Power supply 526 supplies the voltage gradient between the test compound source 530 and optional reservoir 510 via electrodes 528 and 530, respectively. In order to prevent the test compounds from electrokinetically flowing through channel 506a, into optional channel 508 and into reservoir 510, channel 508 is typically configured to present no electroosmotic potential when exposed to an electric field, i.e., electroosmotic flow is substantially absent within the fluid-filled channel, when exposed to an electric field. The elimination of electroosmotic flow in channel 508 is optionally accomplished by a number of methods. For example, channel 508 may be treated differently from channel 506a, so as to mask any surface charge in the channel that might give rise to electroosmotic flow. A variety of surface coatings have been described in the capillary electrophoresis art for eliminating electroosmotic flow in silica capillaries, and such methods are equally applicable to the devices described herein. See, e.g., Lopez et al., J. Am. Chem. Soc. (1993) 115:10774, Bruin et al., J. Chromatog. (1989) 471:429, Townes et al. J. Chromatog. (1990) 516:69. Other surface treatments are also optionally employed, e.g., covalent modification of functional groups at the surface of the channel, such as silanization reactions.

When used to perform, e.g., cell rolling assays, typically at least a portion of channel 506 is provided with an appropriate binding group immobilized to the interior channel surface. Detection window 524 is then used to obtain images of cells traveling along the channel 506. Alternatively, a second detection window (not shown) is provided upstream of detection window 524, for first detecting the cells or group of cells that are being monitored. The cells or groups of cells are then detected at window 524, and their travel time from one point to the other is determined. The velocity f the cells through the binding region of the channel is then used as a measure of the relative level of cellular adhesion to the binding moieties in the channel. The various test compounds are then added to determine their effects, if any, on that velocity.

Alternatively, optional channel 508 is optionally provided with an ion permeable barrier or plug, e.g., a salt bridge, which allows current, but not fluid, to pass. Such plugs include, e.g. gel plugs that are polymerized in situ, e.g., through photopolymerization, and which prevent fluid flow, while permitting the passage of current. Such a configuration permits the sample accessing capillary 504, and channel 506a to operate in conjunction with the electrical control system to create an electroosmotically driven pressure pump. Examples of electroosmotic pressure pumps that are particularly useful in this regard are described in commonly owned U.S. patent application Ser. No. 08/937,958, filed Sep. 25, 1997, which is incorporated herein by reference. Similarly, the use of salt bridges in microfluidic systems is described in published International Application No. 98/00231, which is incorporated herein by reference.

Although the masked surface charge prevents fluid from flowing along channel 508, it does not prevent the tapping of the electrical current from channel 506a into channel 508. The cell suspension is deposited in reservoir 514 and allowed to flow along the analysis channel 506, in the absence of any electrical current. Specifically, by tapping the current upstream of the cell suspension, e.g., into reservoir 510 via channel 508, it prevents the cell suspension from being exposed to the electrical current. Because fluid cannot readily flow along channel 508, the pressure induced by the electroosmotic pumping of the fluid within capillary 504 and channel 506a forces the fluid, including the test compound, to flow into the analysis channel 506. The pressure resulting from the electroosmotic pumping of the electropipettor also ensures that the cell suspension flows along the analysis channel in the direction from the suspension reservoir 514 to the waste reservoir 518, and past detection window 524. In alternative aspects, the electroosmotic pressure pump is provided within the interior portion of the device 500. For example, optional channel 520 and reservoir 522 may be provided in fluid communication with channel 506a downstream of the detection window, e.g., at a point between the detection window and channel 516/reservoir 518. Channel 520 and reservoir 522 are provided in place of channel 508 and reservoir 510, and perform the same function of these elements in the same manner. Specifically, electrode 530 may be contacting the fluid in reservoir 522, while electrode 528 contacts the fluid in reservoir 518. The voltage gradient is then applied to such that fluid is electroosmotically drawn into reservoir 518. Because channel 520 is configured so as to prevent electroosmotic flow of fluid, e.g., as described for channel 508, above, the fluid drawn into reservoir 518 is pulled from analysis channel 506. Again, this type of electroosmotic pressure pump/aspirator is described in U.S. patent application Ser. No. 08/937,958, filed Sep. 25, 1997, incorporated herein by reference.

Although illustrated as a single channel and accessing capillary, it will be readily appreciated that these aspects may be provided as multiple parallel analysis channels and accessing capillaries, in order to substantially increase the throughput of the system. Specifically, single body structures may be provided with multiple parallel analysis channels coupled to multiple sample accessing capillaries that are positioned to sample multiple samples at a time from sample libraries, e.g., multiwell plates. As such, these capillaries are generally spaced at regular distances that correspond with the spacing of wells in multiwell plates, e.g., 9 mm centers for 96 well plates, 4.5 mm for 384 well plates, and 2.25 mm for 1536 well plates.

The present invention is further illustrated with reference to the following non-limiting examples.

EXAMPLES

The following non-limiting examples are provided as being illustrative of the methods, devices and systems of the present invention. The full scope of the present invention, however, is defined only by the literal and equivalent scope of the appended claims.

Example 1

Dual Label Cell Function Assay Methods

The assay methods of the invention were demonstrated in CHO and THP-1 cells, screened against known agonists of calcium transport for these cells.

Cell Culture—Cells (CHO or THP-1) were obtained from the ATCC. THP-1 cells were cultured in RPMI 1640 media containing 10% fetal bovine serum (FBS), sodium pyruvate (1 mM), L-glutamine (2 mM), Penicillin-G/Streptomycin (100 u/ml, 100 $\mu$/ml), beta-mercaptoethanol (50 $\mu$M), HEPES buffer, pH 7.4 (10 mM). CHO cells were cultured in Ham's F12 media containing 10% FBS, L-glutamine (2 mM), and Penicillin-G/Streptomycin (100 u/ml/100 $\mu$g/ml). The cells were maintained by splitting every 3–4 days.

Dye Loading of Cells—The cells were loaded with Fluo-3-AM dye (Molecular Probes) using a 4 $\mu$M solution of the dye in Hank's Balanced Salt Solution (HBSS) containing calcium and magnesium but lacking phenol red. Added to the HBSS were 1% FBS, 2.5 mM probenecid, 30 mM HEPES, pH 7.0, and 0.05% pluronic acid. The cells were incubated in the dye containing solution at approximately, 5–9×10$^6$ cells/5 ml for 50 minutes in a $CO_2$ incubator at 37° C. At the end of the incubation, Syto-17, a nucleic acid staining dye (Molecular Probes), was added at 1 $\mu$M, and cells were further incubated for 10 minutes at room temperature. The dye loaded cells were washed free of excess dye using two washes by centrifugation at 300×g and resuspension in 5 mls of HBSS containing bovine serum albumin (BSA, 1 mg/ml), probenecid (2.5 mM), and HEPES buffer, pH 7 (20 mM). The washed cells were resuspended into Cell Assay Medium. The assay medium for CHO cells was HBSS containing bovine serum albumin (BSA, 1 mg/ml), probenecid (2.5 mM), and HEPES buffer, pH 7.4 (30 mM) and PVA (0.001%). The resuspended cells were then mixed with ficoll-hypaque (2:1 cells:hypaque). For THP-1 cells, the assay medium contained sucrose (8.5%), dextrose (0.3%), HEPES buffer, pH 7.5 (30 mM), NaCl (16 mM), $MgCl_2$ (1 mM), $CaCl_2$ (1 mM), BSA (10 mg/ml), Probenecid (2.5 mM), and polyvinyl alcohol (PVA 90,000 avg. mol. wt., 0.001%). The final density of the cell suspension was 10×10$^6$ cells/ml. The cells were stored at room temperature until used for testing.

Figure 12:
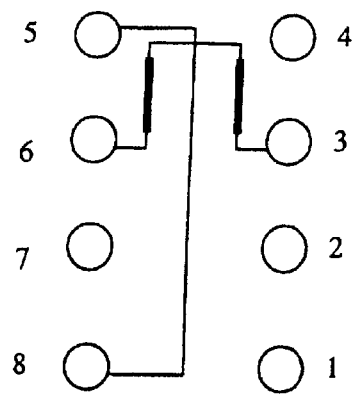
FIG. 12 is a diagram of a microfluidic device used in demonstrating the assay methods of the present invention.

On-Chip Cell Analysis—A microfluidic device having the channel geometry shown in FIG. 12 was used in performing the assay. The channels of the device were rinsed with PVA at 0.2% in cell culture grade water by allowing the solution to wick into the dry device by capillary action and aspirating additional solution through the channels. The PVA solution was displaced with Cell Assay Medium by aspiration through the channels of the device.

The fluid path which the cells followed during the testing was from well #5 to well #3 in the device. The cells were applied in 10 $\mu$l to well #5 and the test sample was applied in 10 $\mu$l to well #6. Both cells and sample flowed into the fluid channel moving toward well #3. Cell Assay Medium (10 $\mu$l) was added to well #8, and well #3 was empty. The fluid continuously moved down the hydrodynamic gradient from wells 5, 6, and 8 into well 3. The ratio of mixing was estimated to be 1/3 sample, 1/6th Assay Medium, and 1/2 cell volume from the measurement of an indicator fluorescent dye before and after mixing with the cell and medium fluid streams. During the time course of the typical test (10–20 minutes), the fluid heights do not change significantly; therefore, the pressure gradients do not change during the course of the test. Some variation in flow velocity was observed during the testing which appeared to be due to the partial filling of the empty waste well causing decreased wicking at the channel exit, in-turn causing decreased flow rate.

The fluorescence of the cells was measured using two PMT's on a Nikon inverted microscope and fluorescein/texas red filter sets (Fluo-3: Ex. max=506, Em. max=526 & Syto-17: Ex. max=621, Em. max=634 nm) for two color analysis. Using the combination of Fluo-3 and Syto-17 dyes, there was no interference by fluorescence quenching of one dye's emission by the other dye. It was, therefore, possible to measure these two indicators simultaneously. The Syto-17 stains all THP-1 or CHO cells similarly because it is permeable to the cell membrane and selective for both RNA and DNA binding. Syto-17 was therefore an indicator of cell density in the reading area. Fluo-3's fluorescence is enhanced by calcium, and, therefore, is a measure of intracellular calcium concentration. The cellular fluorescence was measured in a reading window covering 50 $\mu$m of the channel length and the entire width of the channel (100 $\mu$m) at a distance down-stream of the point of sample addition that was traversed by cells in 10 seconds. The fluorescence was monitored during the test for 100 seconds, during which time approximately 3,300 cells pass the detection window. The sampling rate of the PMT's was 20 hertz and the time constant of sampling was 5 msec., generating about 2000 data points within the 100 second reading interval.

Example 2

Application of Dual Label Cell Function Assay in Dose Response Determination of CHO Cells to Ionomycin Addition CHO cells prepared as described above, were flowed through the analysis channel (between wells 5 and 3) and were contacted with different concentrations of ionomycin, a calcium ionophore (0, 1 $\mu$M, 3 $\mu$M, 10 $\mu$M and 30 $\mu$M) that were introduced from well 6, in separate experiments. Scatter plots from each of these separate experiments are shown in FIGS. 11A–11E. As shown, the amount of intracellular calcium within the cells was readily detected with increasing concentrations of ionomycin. In particular, the slope of the best fit line for the scatter plots increases with increasing ionomycin concentration.

Figure 11A:
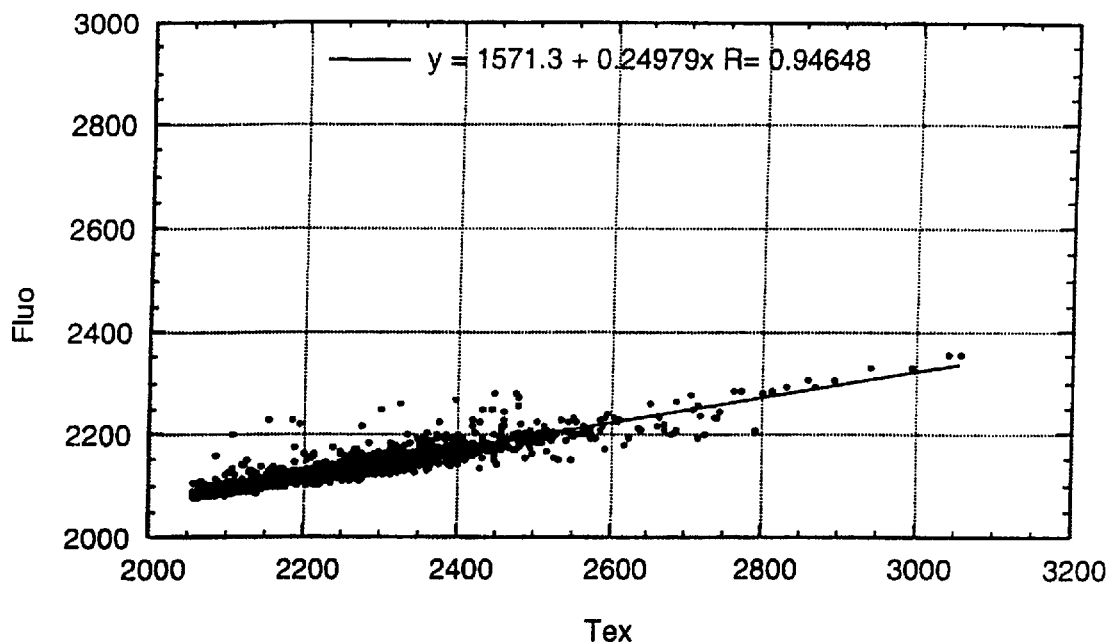
FIGS. 11A–11E show a number of scatter plots of CHO cells stained with Syto-17 (a nucleic acid stain) and with an intracellular calcium indicator (Fluo-3), both in the absence (11A) and presence of varying levels of ionomycin (11B–11E), a known ionophore for calcium that causes increases in intracellular calcium levels.
Figure 11B:
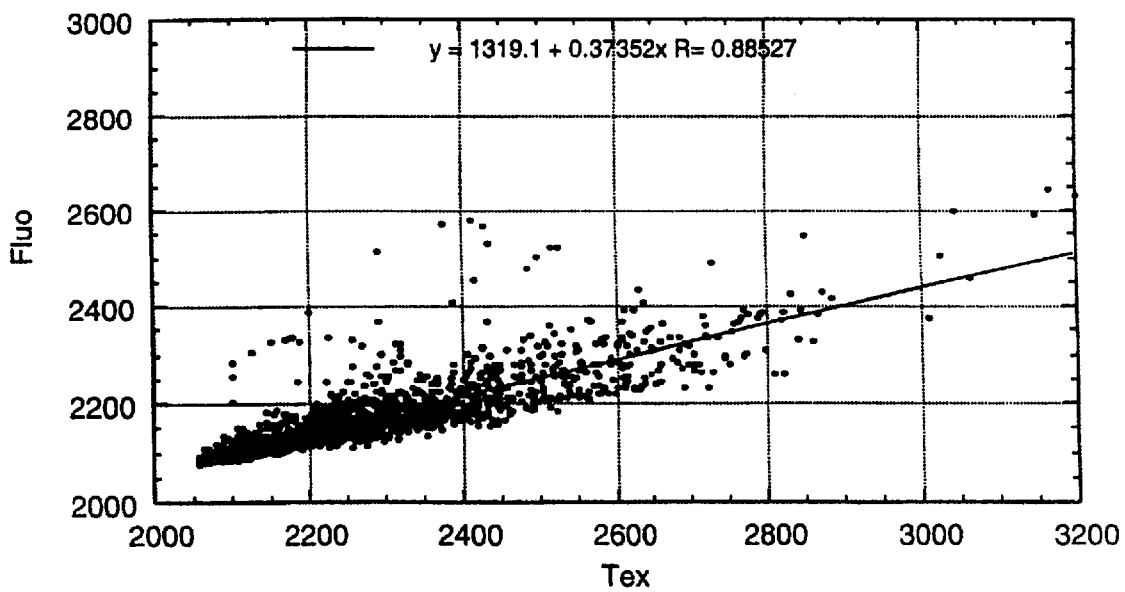
Figure 11C:
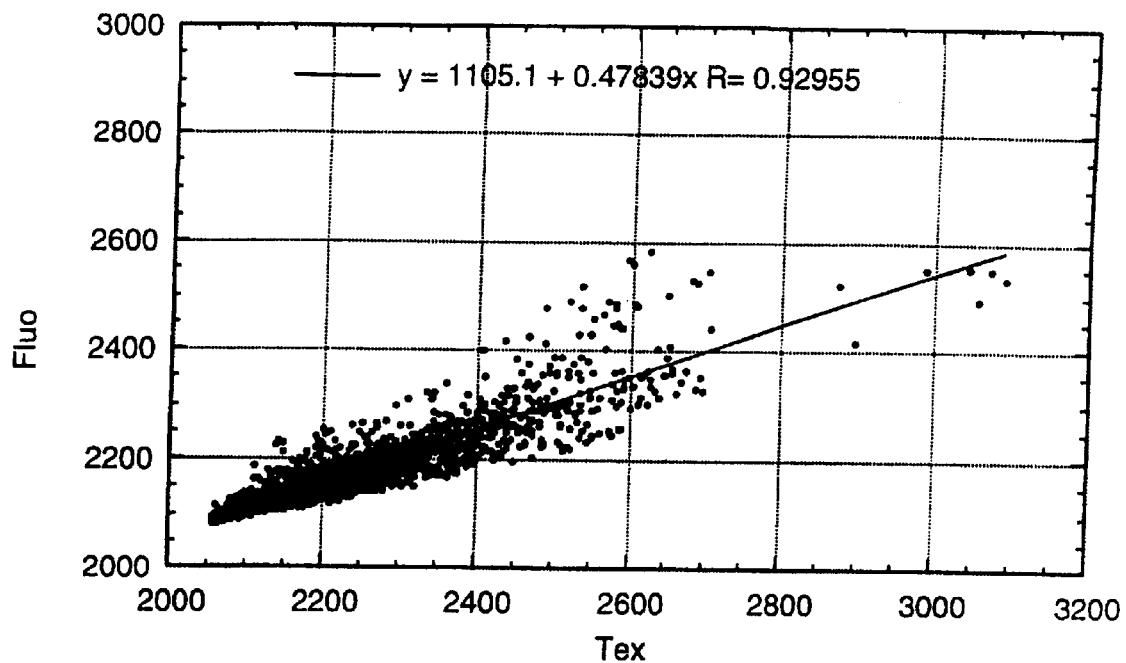
Figure 11D:
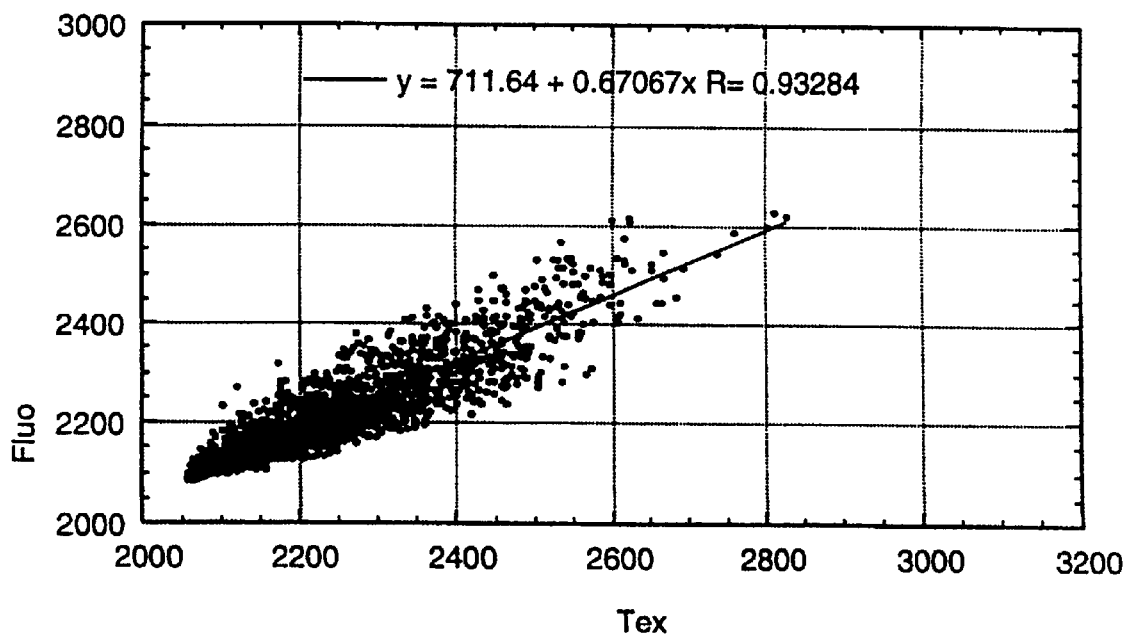
Figure 11E:
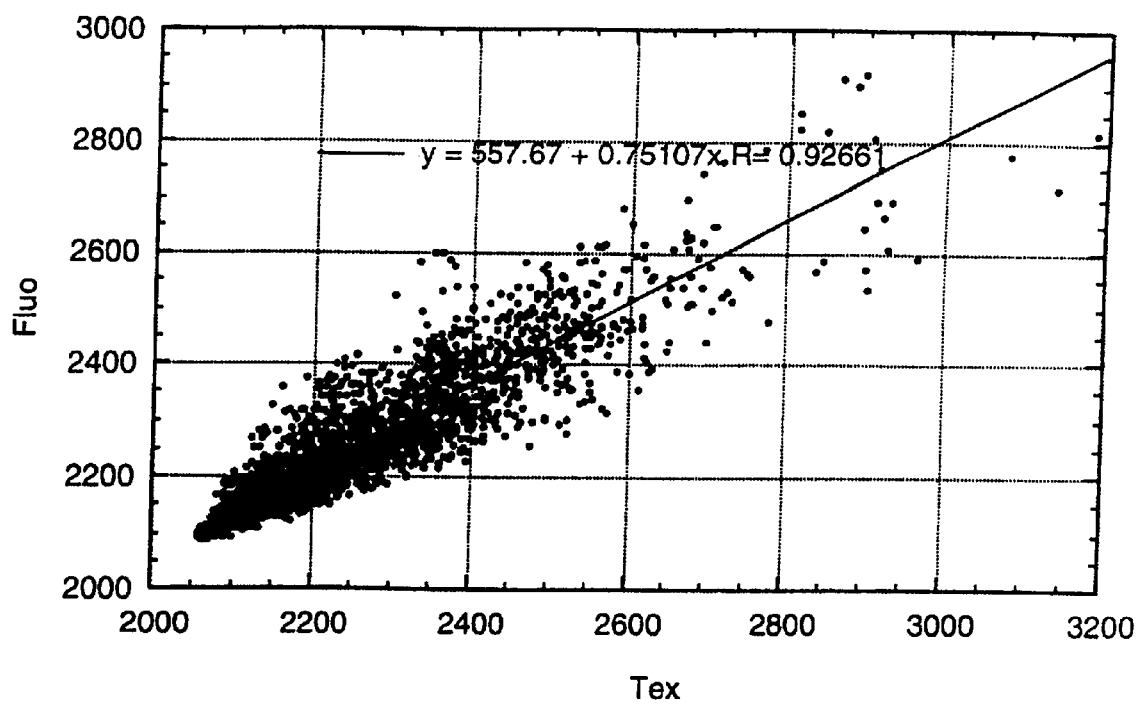
Figure 11F:
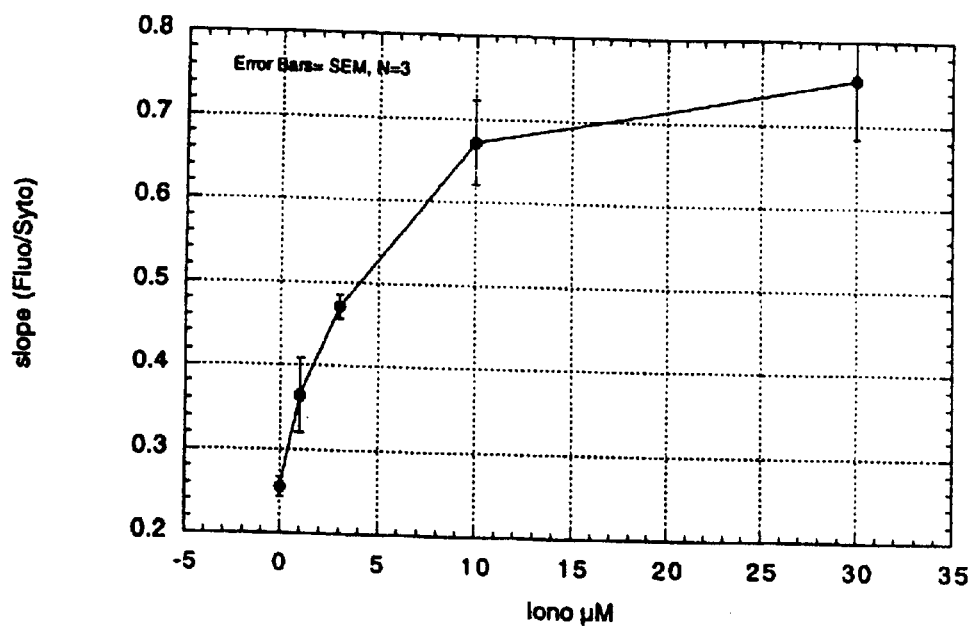
FIG. 11F shows a dose response curve for ionomycin in CHO cells.

FIG. 11F shows a dose response curves for ionomycin in CHO cells, plotting the best fit slope (from FIGS. 11A–11E) versus ionomycin concentration. The slope corresponds to the ratio of calcium modulated fluorescence to cell number and is, therefore, a measure of intracellular calcium concentration. As expected, the intracellular calcium concentration and slope increase with increasing concentrations of ionomycin. Accordingly, these experiments dramatically demonstrate the efficacy of the dual label methods of the present invention for monitoring relative levels of a particular cellular function, i.e., that result in changes in intracellular calcium concentration.

Example 3

Application of Dual Label Cell Function Assay in Dose Response Determination of THP-1 Cells to UTP THP-1 Cells are acute monocytic leukemia cells that can be propagated in culture and maintain the expression of purinergic, P2Y receptors. These G protein-coupled receptors are activated by UTP, ATP, UDP, & ADP and are coupled to cellular Gq mediated calcium signaling pathways. THP-1 cells loaded with a calcium sensitive dye, Fluo-3, were used in this portion of the experiment, and the calcium response of these cells to UTP was detected.

Figure 13:
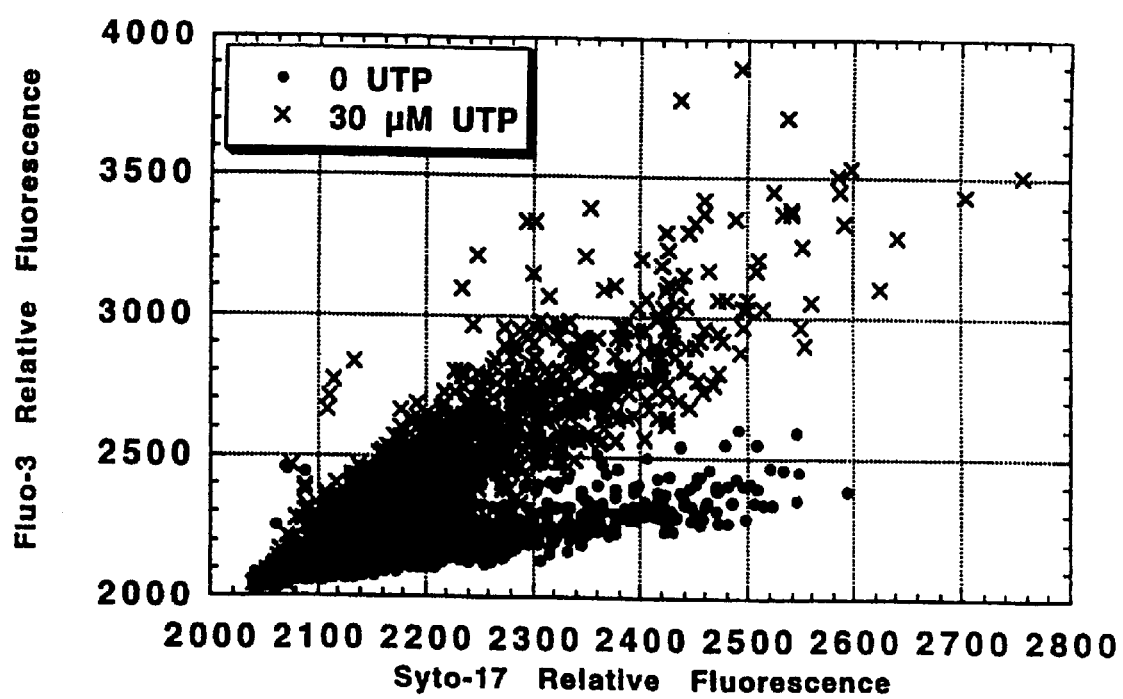
FIG. 13 is a scatter diagram of THP-1 cells bearing a reference label (Syto-17-nucleic acid dye) and a function label (Fluo-3-intracellular calcium indicator). The lower group of plotted points correspond to the control cells while the upper group of plotted points corresponds to cells in the presence of UTP, a known agonist of P2Y receptors that are coupled to intracellular release of calcium stores by the Gq signal transduction pathway.

FIG. 13 shows the data collected from tests using no UTP (lower group of plotted points) and another test using 30 $\mu$M UTP as sample (upper group of plotted points). The scatter plot indicates that the ratio of the Fluo-3 and Syto-17 fluorescence (the slope determined by linear regression) changes with treatment with UTP, an agonist for the P2Y receptor on THP-1 cells.

Figure 14:
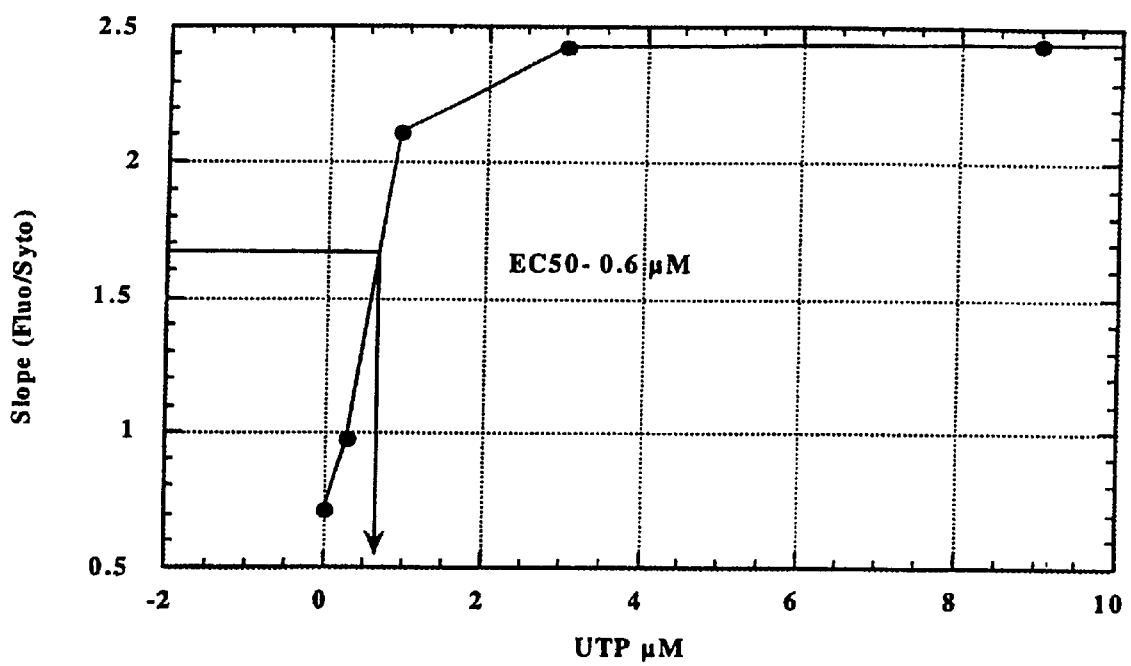
FIG. 14 is a plot of the dose response of intracellular calcium flux in THP-1 cells to varying levels of UTP.
Figure 15:
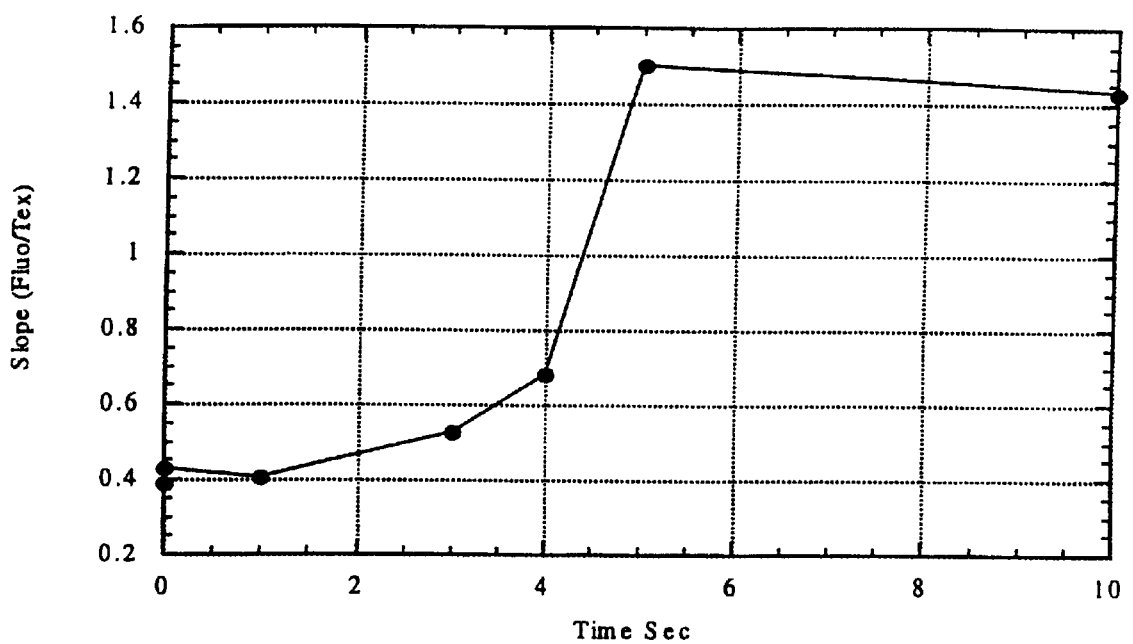
FIG. 15 is a plot of the kinetics of the stimulation of calcium transport with UTP. In particular, intracellular calcium levels are measured as a function of time from contact with UTP, by varying the distance between the detector and the point at which UTP was introduced into the analysis channel.

Results using UTP Treatment of THP-1 Cells—A Concentration Response Curve was generated using the On-Chip Cell Analysis system, treating the THP-1 cells with increasing concentrations of UTP, and is shown in FIG. 14. Kinetic data can also be generated using the On-Chip Cell Analysis System by moving the fluorescence measurement point closer or further from the point of sample addition. This changes the time of incubation with test sample prior to measurement of calcium fluorescence. A shown in FIG. 15, using THP-1 cells and 10 $\mu$M UTP treatment, the calcium response rapidly peaks within 5 seconds of sample introduction.

Example 4

User-editable of Analysis Parameters, Dye Peak Parameters and Manual Dye Settings In one embodiment of the invention, graphical user interface (GUI) windows can be accessed to allow a user to edit analysis parameters, dye peak parameters and manual dye settings. In general, these windows give a user control over finding dye peaks, fine tuning of finding cell events and calculating ratios of normalized event signals. Typically, the values in the windows are saved to a data file for subsequent usage by the program.

Figures 16A, 16B:
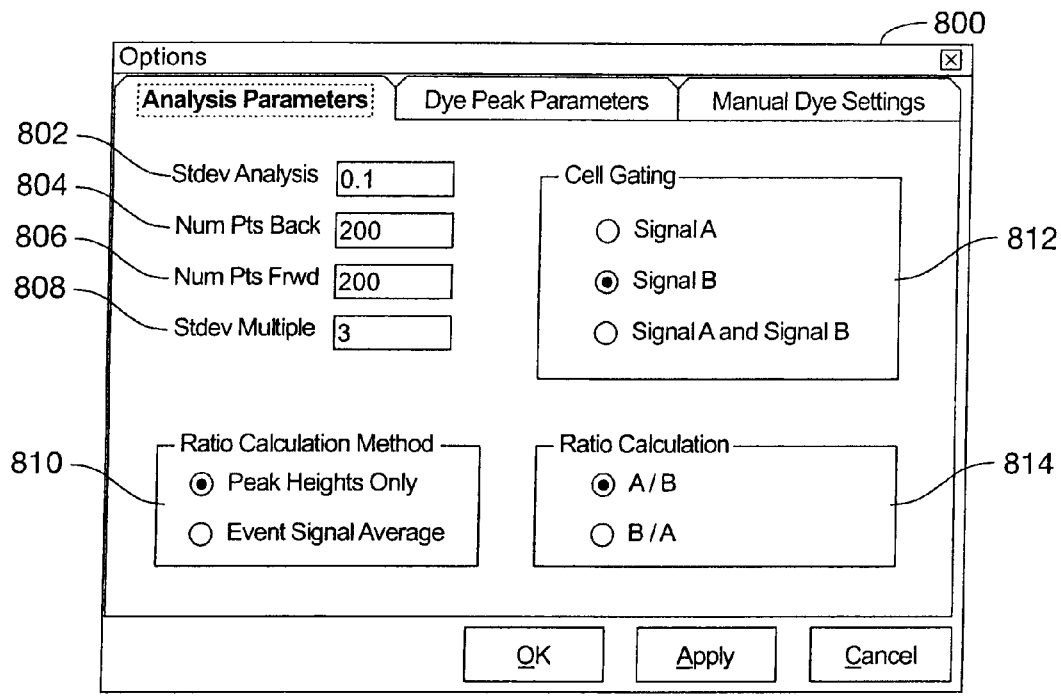
FIGS. 16A–16C show examples of windows that allow users to edit analysis parameters, dye peak parameters and manual dye settings.

FIG. 16A shows an example of a window that allows a user to edit analysis parameters. A window 800 includes a variety of GUI controls such as tabs, radio controls, text boxes, and buttons. A text box 802 allows a user to specify the standard deviation to be utilized for the baseline in displayed graphs of the data. Typically, a lower standard deviation value should be entered for noisier data.

In some embodiments, the peak find and baseline estimation is accomplished utilizing a moving average. Text boxes 804 and 806 allow a user to specify the resolution of this moving average by specifying the number of data points back and forward, respectively, the moving average should include. The lower the values, the smaller the window of data points that are used, which means that the moving average will be more sensitive to the data. A text box 808 allows a user to enter a standard deviation multiple value for cell events. This is the multiple of the standard deviation that is required to identify a cell event for calculating ratios.

Radio controls 810 allow a user to specify the way in which the ratio calculation will be performed. The user is able to select the utilization of peak heights or event signal averages. Radio controls 812 allow a user to specify cell gating as signal A, signal B or signals A and B. Lastly, radio controls 814 allow a user to specify whether the ratio is calculated as A/B or B/A. In the embodiment described, there are two signals, A and B, corresponding to two channels. Other embodiments can have more or fewer channels and signals.

FIG. 16B shows an example of a window that allows a user to edit dye peak parameters. A window 830 includes a text box 832 allows a user to specify the standard deviation multiple value for dye peaks. A text box 834 allows a user to specify the peak multiple, which will be utilized to identify the dye peaks (see the example in the next section for an illustration of the operation of this parameter). A number of samples between dye peaks can be entered in a text box 836. In some embodiments, the number of samples between dye peaks is determined when the data is received or read in, however, a user may specify a different value, desired.

A text box 838 allows a user to specify shift assigned times. The shift assigned times will shift all the data times to the left or right on displayed graphs the specified number of seconds (negative values shift to the left and positive values shift to the right). The text boxes 840, 842 and 844 allow a user to specify how the moving average for dye peaks will be calculated. The number of data points backward and forward can be specified as long as a number of data points to be utilized for smoothing.

Figure 16C:
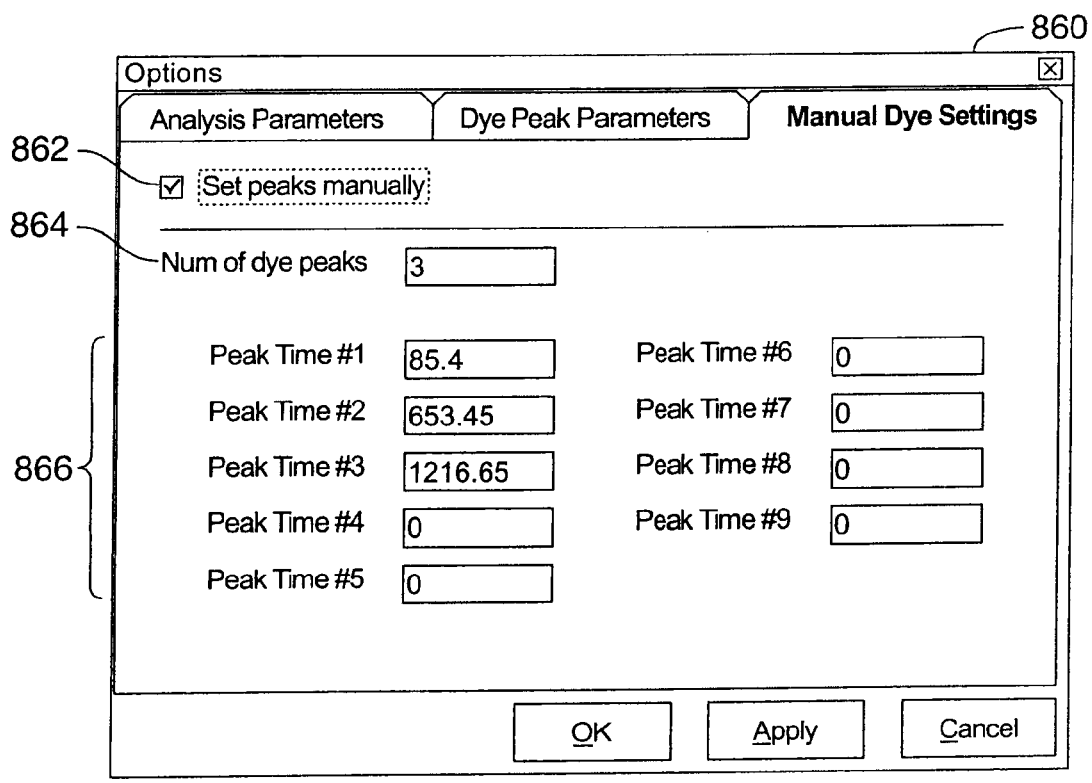

FIG. 16C shows an example of a window that allows a user to edit manual dye settings. A window 860 includes a check box 862 that allows a user to set the peaks manually (i.e., instead of having the program set the peaks). A text box 864 allows a user to select how many peaks can be edited in a dialog box 866. As indicated, dialog box allows a user to specify the peak time for the number of peaks that are set by the user manually.

Example 5

Dye Peak Identification

A described above, a user in one embodiment can specify one or more parameters for identifying dye peaks. This example will illustrate the effect of the peak multiple that can be specified in text box 834 of FIG. 16B.

Figure 17A:
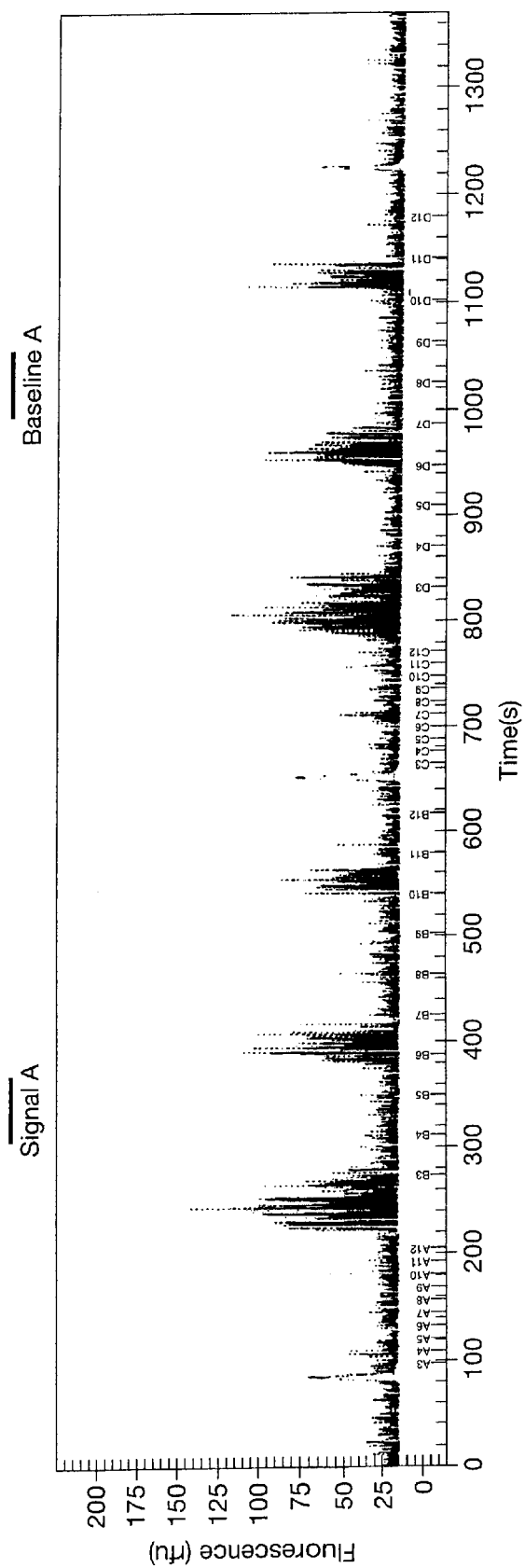
FIGS. 17A–17C show examples of graphs that illustrate the effect of dye peak parameters on identified dye peaks.

In this example, there are three dye peaks, one before samples A3–A12, one between samples A3–A12 and B3–B12, and one after samples B3–B12. FIG. 17A shows a graph of signal A that has the peak multiple value set too low because there were five dye peak identified (see that samples for A3–12, B3–B12, C3–C12, and D3–D12 are specified on the x-axis of the graph shown).

Figure 17B:
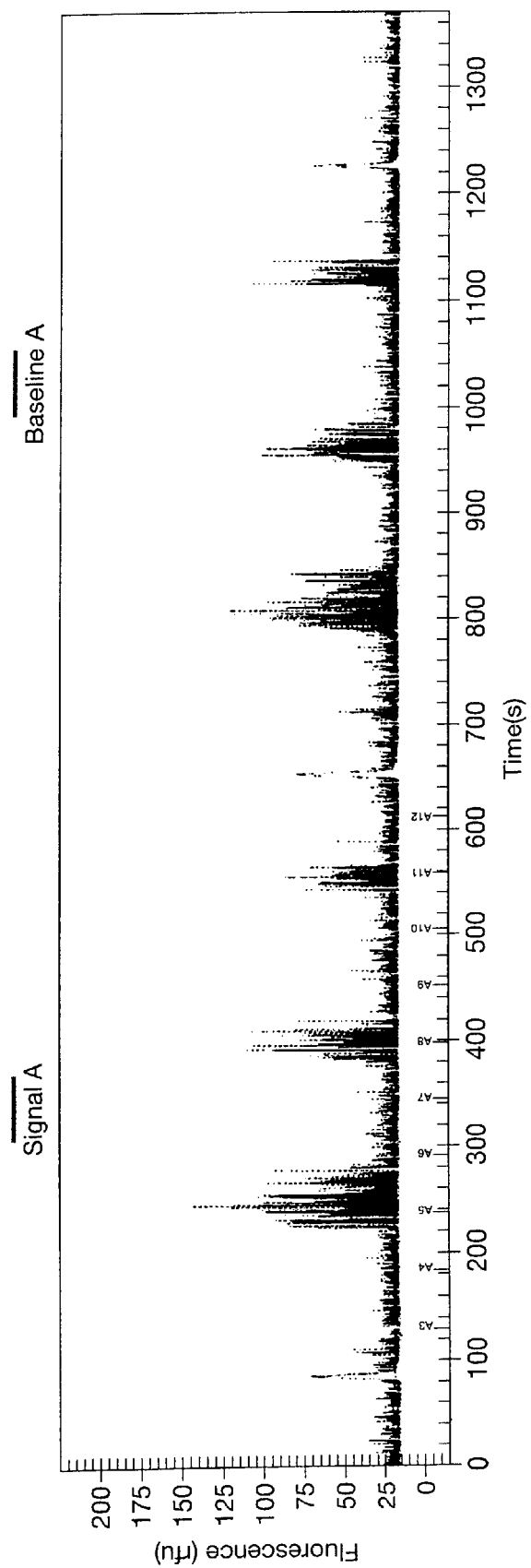
Figure 17C:
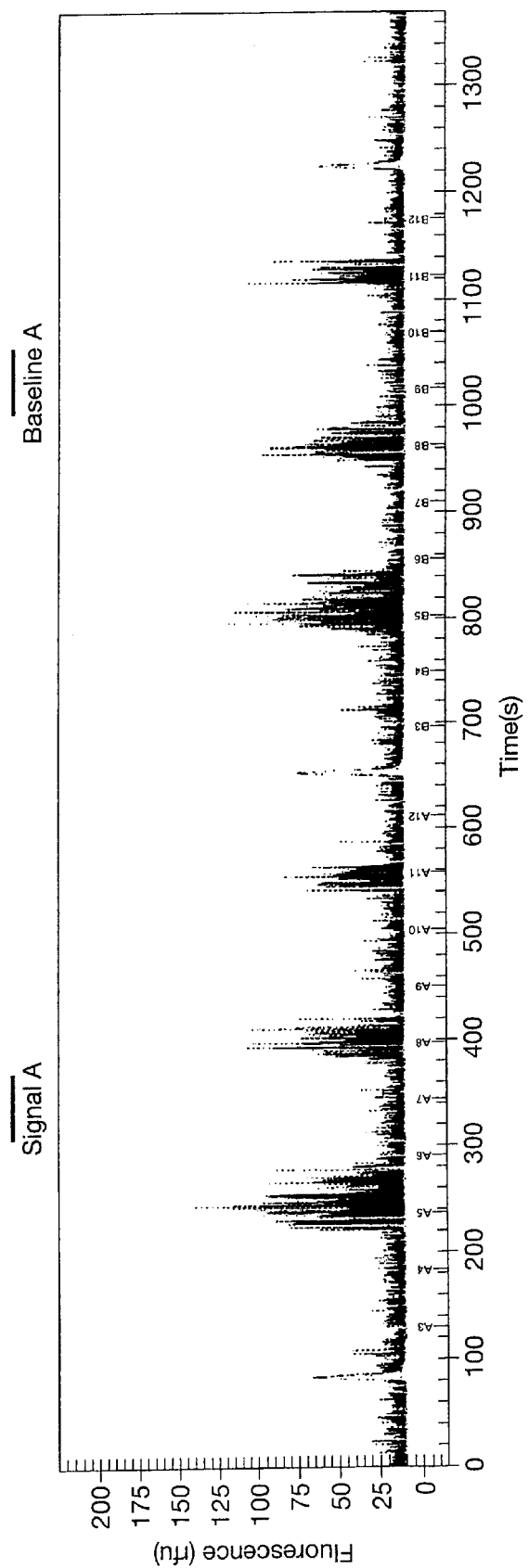

If the peak multiple value is set too high, too few dye peaks will be identified. FIG. 17B shows that there were only two dye peaks identified (see that only samples for A3–12 are specified on the x-axis of the graph shown). As FIG. 17C illustrates, if the correct peak multiple value of 0.5 is specified, the correct number of dye peaks (three) are identified as indicated by samples A3–A12 and B3–B12 being specified on the x-axis of the graph.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A computer implemented method of determining a level of function of cells, comprising:

receiving first signals corresponding to a first detectable property of the cells in a suspension flowing along a fluid channel;

receiving second signals corresponding to a second detectable property produced by the cells upon activation of the function of the cells; and determining the level of the function of the cells by comparing the first and second signals.

2. The method of claim 1, wherein comparing the first and second signals includes calculating a ratio of the first and second signals, the ratio being indicative of the level of function of the cells.

3. The method of claim 1, further comprising displaying the level of the function of the cells to a user.

4. The method of claim 1, wherein the first and second signals are received simultaneously.

5. The method of claim 1, wherein the fluid channel includes a test compound, wherein the level of function of the cells is determined in the presence of the test compound.

6. The method of claim 5, further comprising determining an effect of the test compound on the level of the function of the cells by comparing the level of the function of the cells to a reference level of function of the cells.

7. The method of claim 5, further comprising displaying the effect of the test compound to a user.

8. The method of claim 5, further comprising introducing the test compound into the fluid channel.

9. The method of claim 1, wherein the fluid channel includes a plurality of different test compounds, wherein the level of function of the cells is separately determined in the presence of each of the different test compounds.

10. The method of claim 9, further comprising determining an effect of each different test compound on the level of the function of the cells by comparing the level of the function of the cells to a reference level of function of the cells.

11. The method of claim 9, further comprising displaying the effect of each of the different test compounds to a user.

12. The method of claim 9, further comprising introducing the different test compounds serially into the fluid channel.

13. The method of claim 1, further comprising applying a pressure differential along the fluid channel to flow the suspension of cells along the fluid channel.

14. The method of claim 1, further comprising applying an electric field along a length of the fluid channel, the electric field being sufficient to cause electrokinetic flowing of the suspension of cells along the fluid channel.

15. The method of claim 1, further comprising applying an inertial force to the suspension of cells to cause the suspension of cells along the fluid channel.

16. The method of claim 1, further comprising measuring the first and second detectable properties of the cells.

17. The method of claim 16, wherein the first and second detectable properties of the cells are measured simultaneously.

18. The method of claim 1, wherein the function of the cells is selected from binding functions, transport functions, expression functions, and viability.

19. A computer program product for determining a level of function of cells, comprising:

computer code that receives first signals corresponding to a first detectable property of the cells in a suspension flowing along a fluid channel;

computer code that receives second signals corresponding to a second detectable property produced by the cells upon activation of the function of the cells;

computer code that determines the level of the function of the cells by comparing the first and second signals; and a computer readable medium that stores the computer codes.

20. The computer program product of claim 19, wherein the computer readable medium is a CD-ROM, floppy disk, tape, flash memory, system memory, hard drive, or data signal embodied in a carrier wave.

21. A system, comprising:
a microfluidic device having a fluid channel;
at least one detector for measuring at least one detectable property in the fluid channel; and
a computer system that controls the flow of a suspension of cells along the fluid channel and receives signals from the at least one detector, the computer system executing a program stored on a computer readable medium comprising:
computer code that receives first signals corresponding to a first detectable property of the cells in a suspension flowing along a fluid channel;
computer code that receives second signals corresponding to a second detectable property produced by the cells upon activation of the function of the cells; and
computer code that determines the level of the function of the cells by comparing the first and second signals.

22. The system of claim 21, wherein the computer readable medium is a CD-ROM, floppy disk, tape, flash memory, system memory, hard drive, or data signal embodied in a carrier wave.

23. A computer implemented method of determining a binding function of cells, comprising:
receiving first signals corresponding to a detectable property of the cells in a suspension flowing along a binding region of a fluid channel in the presence of a test compound, the binding region having a binding moiety immobilized on an interior surface of the fluid channel and the cells including on their surfaces a moiety bound by the binding moiety;
calculating a velocity of the cells flowing through the binding region by analyzing the first signals; and
determining an effect of the test compound on the binding function of the cells by comparing the velocity to a reference velocity.

24. The method of claim 23, wherein the reference velocity is of the cells flowing along the binding region of the fluid channel in the absence of the test compound.

25. The method of claim 24, wherein the fluid channel includes a non-binding region having substantially no binding moiety immobilized therein.

26. The method of claim 25, further comprising:
receiving second signals corresponding to the detectable property of the cells in the suspension flowing along the non-binding region of the fluid channel in the presence of the test compound; and
calculating the reference velocity by analyzing the second signals.

27. The method of claim 23, further comprising flowing the suspension of cells along the fluid channel.

28. The method of claim 27, wherein flowing the suspension of cells along the fluid channel includes pulsing groups of cells through the fluid channel.

29. The method of claim 27, wherein flowing the suspension of cells along the fluid channel includes applying a pressure differential across the length of the fluid channel.

30. The method of claim 29, wherein applying the pressure differential includes applying a hydrostatic pressure to one end of the fluid channel.

31. The method of claim 29, wherein applying the pressure differential includes applying an electroosmotically driven pressure to one end of the fluid channel.

32. The method of claim 23, wherein calculating a velocity of the cells flowing through the binding region includes:
determining a time difference between when the first signals indicate the cells passed first and second points on the fluid channel, the first and second points being spaced apart along the fluid channel; and
calculating the velocity from the time difference and a distance along the fluid channel between the first and second points.

33. The method of claim 23, further comprising introducing the test compound into the fluid channel.

34. The method of claim 23, further comprising displaying the effect of the test compound on the binding function of the cells to a user.

35. The method of claim 23, wherein the effect is that the test compound is an inhibitor of the binding function of the cells if the velocity is less than the reference velocity and the effect is that the test compound is an enhancer of the binding function of the cells if the velocity is less than the reference velocity.

36. The method of claim 23, further comprising determining effects of a plurality of different test compounds on the binding function of the cells by analyzing velocities of cells flowing serially through the binding region in the presence of each of the different test compounds.

37. The method of claim 36, further comprising displaying the effect of each of the different test compounds to a user.

38. The method of claim 36, further comprising introducing the different test compounds serially into the fluid channel.

39. A computer program product for determining a binding function of cells, comprising:
computer code that receives first signals corresponding to a detectable property of the cells in a suspension flowing along a binding region of a fluid channel in the presence of a test compound, the binding region having a binding moiety immobilized on an interior surface of the fluid channel and the cells including on their surfaces a moiety bound by the binding moiety;
computer code that calculates a velocity of the cells flowing through the binding region by analyzing the first signals;
computer code that determines an effect of the test compound on the binding function of the cells by comparing the velocity to a reference velocity; and
a computer readable medium that stores the computer codes.

40. The computer program product of claim 39, wherein the computer readable medium is a CD-ROM, floppy disk, tape, flash memory, system memory, hard drive, or data signal embodied in a carrier wave.

41. A system, comprising:
a microfluidic device having a fluid channel;
at least one detector for measuring at least one detectable property in the fluid channel; and
a computer system that controls the flow of a suspension of cells along the fluid channel and receives signals from the at least one detector, the computer system executing a program stored on a computer readable medium comprising:
computer code that receives first signals corresponding to a detectable property of the cells in a suspension flowing along a binding region of a fluid channel in the presence of a test compound, the binding region having a binding moiety immobilized on an interior surface of the fluid channel and the cells including on their surfaces a moiety bound by the binding moiety;

computer code that calculates a velocity of the cells flowing through the binding region by analyzing the first signals; and computer code that determines an effect of the test compound on the binding function of the cells by comparing the velocity to a reference velocity.

42. The system of claim 41, wherein the computer readable medium is a CD-ROM, floppy disk, tape, flash memory, system memory, hard drive, or data signal embodied in a carrier wave.

* * * * *